US009058375B2

(12) United States Patent
Rosen et al.

(10) Patent No.: US 9,058,375 B2
(45) Date of Patent: Jun. 16, 2015

(54) SYSTEMS AND METHODS FOR ADDING DESCRIPTIVE METADATA TO DIGITAL CONTENT

(71) Applicant: Smart Screen Networks, Inc., San Diego, CA (US)

(72) Inventors: Stephen D. Rosen, San Diego, CA (US); Jeff Symon, Rancho Santa Fe, CA (US); George C. Kenney, San Diego, CA (US); Jorge Sanchez, Poway, CA (US)

(73) Assignee: SMART SCREEN NETWORKS, INC., Encinitas, CA (US)

( * ) Notice: Subject to any disclaimer, the term of this patent is extended or adjusted under 35 U.S.C. 154(b) by 0 days.

(21) Appl. No.: 14/323,738

(22) Filed: Jul. 3, 2014

(65) Prior Publication Data

US 2015/0100578 A1  Apr. 9, 2015

Related U.S. Application Data

(60) Provisional application No. 61/888,513, filed on Oct. 9, 2013.

(51) Int. Cl.
*G06F 17/00* (2006.01)
*G06F 17/30* (2006.01)
*G06F 17/22* (2006.01)

(52) U.S. Cl.
CPC ...... *G06F 17/30598* (2013.01); *G06F 17/2247* (2013.01)

(58) Field of Classification Search
CPC .......... G06F 17/2247; G06F 17/30896; G06F 17/30233; G06F 17/30047; G06F 17/30056

USPC ................... 715/234, 255; 707/609, 736, 825
See application file for complete search history.

(56) References Cited

U.S. PATENT DOCUMENTS

| 7,163,151 | B2 * | 1/2007 | Kiiskinen ................ 235/472.01 |
| 7,634,463 | B1 * | 12/2009 | Katragadda et al. .......... 701/431 |
| 7,797,337 | B2 * | 9/2010 | Fry .............................. 707/776 |
| 8,526,782 | B2 * | 9/2013 | Kaiser et al. .................. 386/240 |
| 8,762,400 | B2 * | 6/2014 | Ivanov et al. ................. 707/758 |

(Continued)

FOREIGN PATENT DOCUMENTS

| JP | 2007140199 A | 6/2007 |
| JP | 2008072572 A | 3/2008 |
| WO | 2004086254 A1 | 10/2004 |

OTHER PUBLICATIONS

Author Unknown, "Panasonic Introduces Video 'Voice Tagging'", PR Newswire, Apr. 7, 2003, 2 pages.

(Continued)

*Primary Examiner* — Laurie Ries
(74) *Attorney, Agent, or Firm* — Procopio Cory Hargreaves & Savitch LLP; Jonathan D. Cheng; Pattric J. Rawlins

(57) ABSTRACT

Methods, computer-readable media, and systems for scheduling the association of metadata with content. In an embodiment, event information is obtained from a virtual calendar, wherein the event information comprises at least one event detail and one or more parameters defining a time period. First metadata is generated based on the event detail, and is stored, in association with the time period, in a memory. Then, subsequently, during the time period, the first metadata may be retrieved from the memory, and associated with one or more content items generated on the device.

26 Claims, 29 Drawing Sheets

(56) References Cited

U.S. PATENT DOCUMENTS

| | | | |
|---|---|---|---|
| 8,832,162 B2* | 9/2014 | Greenspan et al. | 707/825 |
| 8,838,836 B1* | 9/2014 | Li et al. | 709/248 |
| 2003/0126136 A1* | 7/2003 | Omoigui | 707/10 |
| 2004/0010493 A1* | 1/2004 | Kojima et al. | 707/4 |
| 2005/0091576 A1* | 4/2005 | Relyea et al. | 715/502 |
| 2006/0007315 A1 | 1/2006 | Singh | |
| 2006/0075034 A1* | 4/2006 | Lakkala et al. | 709/206 |
| 2006/0148528 A1* | 7/2006 | Jung et al. | 455/566 |
| 2007/0174326 A1 | 7/2007 | Schwartz et al. | |
| 2007/0192358 A1* | 8/2007 | Nagda et al. | 707/102 |
| 2007/0198632 A1* | 8/2007 | Peart et al. | 709/203 |
| 2007/0253678 A1* | 11/2007 | Sarukkai | 386/95 |
| 2008/0168449 A1* | 7/2008 | Rice et al. | 718/102 |
| 2009/0000832 A1* | 1/2009 | Marggraff et al. | 178/19.01 |
| 2010/0207727 A1* | 8/2010 | Kanekiyo et al. | 340/5.82 |
| 2010/0316264 A1* | 12/2010 | Ferren et al. | 382/117 |
| 2011/0040754 A1* | 2/2011 | Peto et al. | 707/736 |
| 2011/0099163 A1* | 4/2011 | Harris et al. | 707/723 |
| 2011/0194028 A1* | 8/2011 | Dove et al. | 348/563 |
| 2011/0289422 A1* | 11/2011 | Spivack et al. | 715/739 |
| 2012/0030240 A1* | 2/2012 | Engelhardt et al. | 707/778 |
| 2012/0035925 A1* | 2/2012 | Friend et al. | 704/235 |
| 2012/0084276 A1* | 4/2012 | Heimendinger | 707/708 |
| 2012/0130762 A1* | 5/2012 | Gale et al. | 705/7.13 |
| 2012/0144407 A1* | 6/2012 | Hacigumus et al. | 719/328 |
| 2012/0284637 A1* | 11/2012 | Boyer et al. | 715/751 |
| 2012/0315881 A1* | 12/2012 | Woloshyn | 455/412.2 |
| 2012/0323890 A1* | 12/2012 | Dixon et al. | 707/722 |
| 2013/0006695 A1* | 1/2013 | Haustein et al. | 705/7.26 |
| 2013/0083208 A1* | 4/2013 | Koh | 348/207.2 |
| 2013/0089300 A1* | 4/2013 | Soundararajan et al. | 386/241 |
| 2013/0129142 A1 | 5/2013 | Miranda-Steiner | |
| 2013/0198197 A1* | 8/2013 | Sawhney et al. | 707/741 |
| 2013/0218858 A1* | 8/2013 | Perelman et al. | 707/706 |
| 2013/0249948 A1* | 9/2013 | Reitan | 345/633 |
| 2013/0282379 A1* | 10/2013 | Stephenson et al. | 704/270 |
| 2013/0318193 A1* | 11/2013 | Koli et al. | 709/213 |
| 2013/0335594 A1* | 12/2013 | Benko et al. | 348/231.4 |
| 2014/0164317 A1* | 6/2014 | Lynch et al. | 707/609 |
| 2014/0304235 A1* | 10/2014 | Rooks et al. | 707/667 |

OTHER PUBLICATIONS

International Search Report and Written Opinion mailed on Jan. 15, 2015 for PCT/US2014/059764 in 8 pages.

* cited by examiner

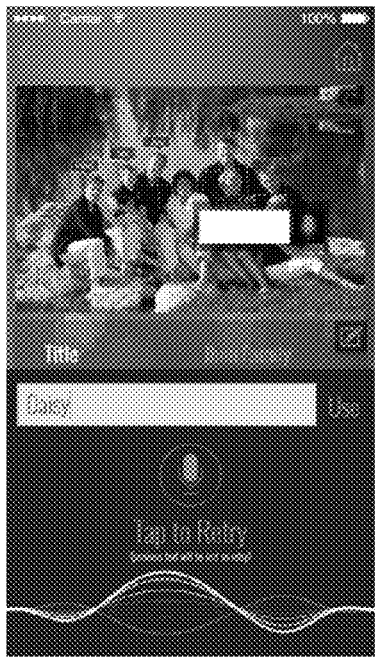
FIG. 13O
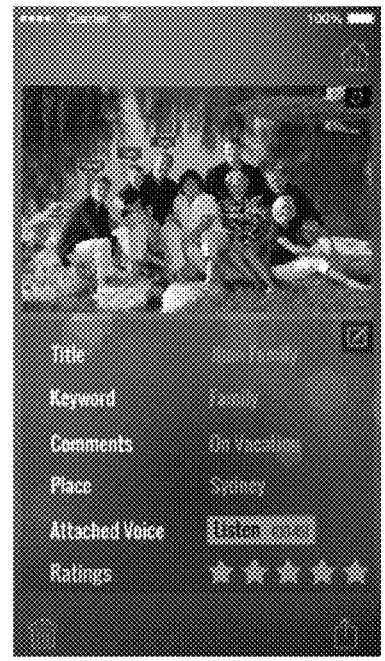
FIG. 13P
FIG. 13Q
FIG. 13R

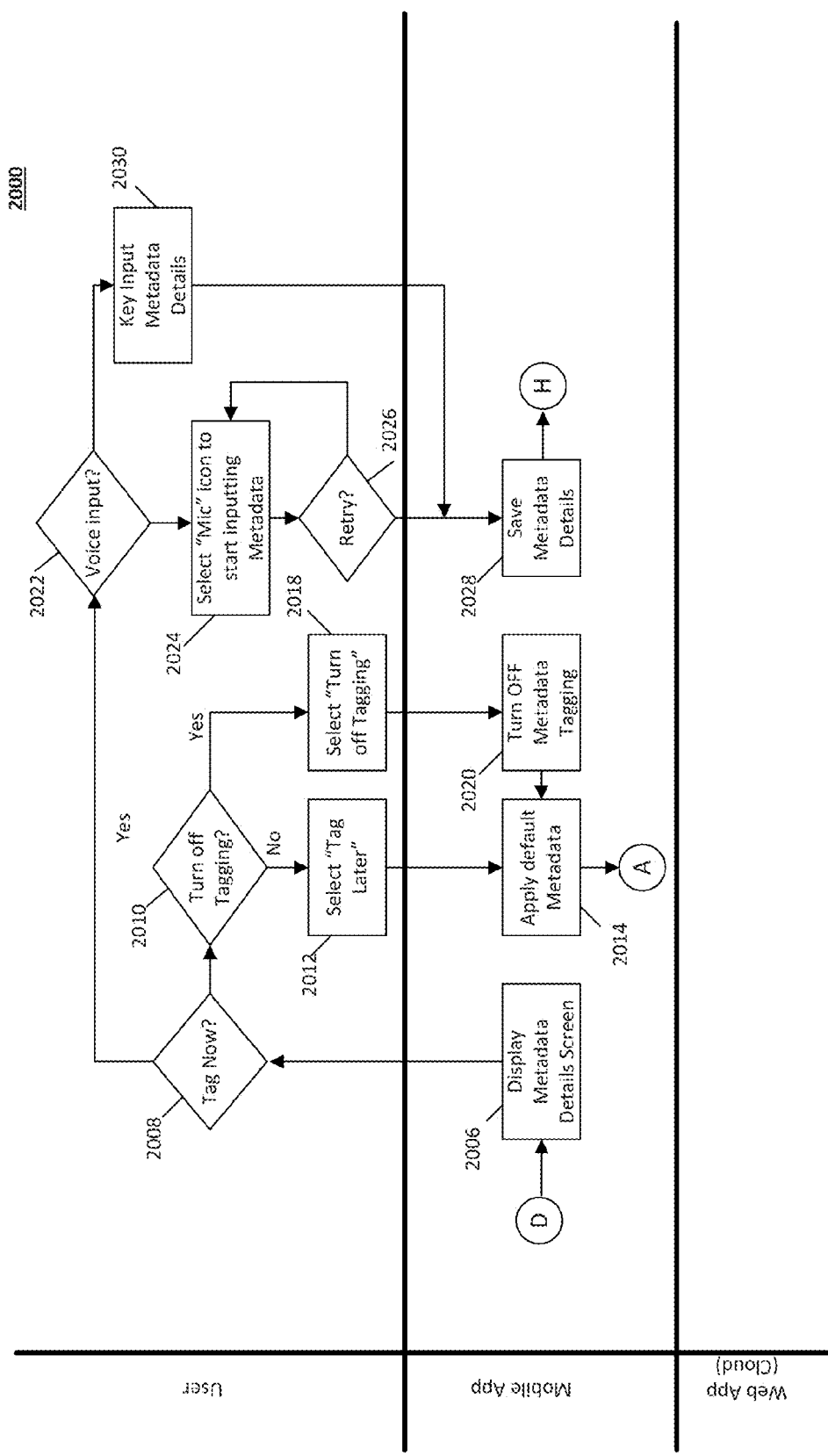

SYSTEMS AND METHODS FOR ADDING DESCRIPTIVE METADATA TO DIGITAL CONTENT

CROSS-REFERENCE TO RELATED APPLICATIONS

This application claims priority to U.S. Provisional Patent App. No. 61/888,513, filed on Oct. 9, 2013, and titled "Intelligent Metadata Management for Classification and Retrieval of Content," the entirety of which is hereby incorporated herein by reference.

BACKGROUND

1. Field of the Invention

The embodiments described herein are generally directed to metadata, and, more particularly, to the manual and/or automatic addition of metadata to media, such as images, video recordings, audio recordings, electronic documents, text, and other types of content.

2. Description of the Related Art

Digital media—generally referred to herein as "content"—can take a variety of forms, including images, video recordings, audio recordings, text, and other forms of data. When content is owned and/or is associated with a right to use, the content may be referred to as a "digital asset." However, as used herein, the term "content" or "content item" (a specific instance of content) includes any type of media, regardless of whether or not it comprises a digital asset.

"Metadata," which is often defined as "data about data," is used herein to designate descriptive or technical information that is embedded in or otherwise associated with the data (e.g., file or files) embodying content. Technical metadata refers to information about the technical properties of the content, such as an identifier of the device that was used to capture the content, a resolution of the content, a timestamp representing the date and time on which the content was created and/or modified, a format of the content, etc. Descriptive metadata, on the other hand, refers to information describing the content, such as the names of individuals who appear in the content, an author or producer of the content, a rating of the content, a narrative description of the content, keywords that are relevant to the content, etc. Descriptive metadata is particularly useful for organizing, categorizing, and searching content. For example, a search engine may be configured to parse the descriptive metadata associated with a content item to determine whether the content item is relevant to a particular search query (e.g., if any text in the descriptive metadata match any keywords in the search query).

Currently, there are a number of commonly-used standards used for storing metadata in association with content. For example, Exchangeable Image File Format (EXIF) is a standard that specifies the formats for images, sound, and ancillary tags used by digital cameras (including smart phones), scanners, and other media-capturing devices. EXIF defines a number of metadata tags or fields into which metadata, including technical and descriptive metadata, can be entered. In EXIF, metadata is embedded within the content file itself. Another example standard is the International Press Telecommunications Council (IPTC) Information Interchange Model (IIM), which has been largely superseded by the Extensible Metadata Platform (XMP). XMP is an open-source standard for the creation, processing, and interchange of standardized and custom metadata for all kinds of resources. XMP can be embedded in many types of file formats, such as JPEG, Tagged Image File Format (TIFF), and Portable Document Format (PDF), but can also be stored separately as a "sidecar" file to content. Generally, metadata stored using these formats comprise copyright information, credits, creation date, creation location, source information, comments, special format instructions, etc.

Whereas technical metadata can generally be automatically created and associated with content (e.g., during creation of the content), descriptive metadata is much less conducive to automatic generation and association. Conventionally, descriptive metadata must be manually entered and associated with content. For example, typically, for each individual content item, a content creator must select the content item and manually enter descriptive metadata to be associated with that content item, using a keyboard, touch pad, or other input device. For individuals or other entities (e.g., entertainment, film production, news, or broadcasting companies) that generate a lot of content, the generation and association of descriptive metadata with the created content can be inefficient, time-consuming, and otherwise burdensome.

For instance, with the advent of smart phones, tablets, and other digital devices and the decreasing cost of storage, the volume of content produced by users in the consumer market has exploded in recent years. A typical user of such devices may produce tens of thousands of content items. Over time, the majority of users do not bother to expend the effort necessary to manually add descriptive metadata to each content item. Furthermore, commonly-available applications, which may provide functions for adding metadata to content, do not provide the ability to add descriptive metadata in bulk. Instead, a user must wade through an ocean of content items and manually add descriptive metadata to each individual content item.

Moreover, conventional applications are not conducive to the addition of metadata in the moment. For example, many users take pictures in social situations, on vacations, during sports events or activities, and/or in other hurried environments, in which it is not convenient or appropriate for the user to stop for the length of time necessary to manually enter metadata. Thus, the entry of metadata is typically significantly delayed. This problem has been exacerbated with the advent of cameras with fast shutters, which can take multiple images per second, and which can produce hundreds of images in a short period of time. Content creators may often find themselves with hundreds or thousands of content items, each with generic names (e.g., assigned by the camera or other device), limited technical metadata, and little or no descriptive metadata.

The burden associated with manually entering metadata and the deficiencies in prior art applications has frustrated the ability of descriptive metadata to keep up with the ever-increasing volume of content that is generated today. In turn, this lack of descriptive metadata hinders the ability to search, organize, and enjoy such content. What are needed are improved processes and systems for adding descriptive metadata to content items. Embodiments should be user friendly, automatic or semi-automatic, and/or capable of being performed in bulk. Such improved processes and systems can facilitate the subsequent organization, sorting, and searching of the content items, thereby improving a user's experience of those content items.

SUMMARY

Accordingly, systems and methods are disclosed for adding descriptive metadata to content items. In an embodiment, a method for scheduling the association of metadata with content is disclosed. The method comprises using at least one hardware processor of a device to: obtain event information from a virtual calendar, wherein the event information comprises at least one event detail and one or more parameters defining a time period; generate first metadata based on the at least one event detail; store the first metadata, in association with the time period, in a memory; and, subsequently, during the time period, retrieve the first metadata from the memory, and associate the first metadata with one or more content items generated on the device. The one or more content items may comprise a plurality of content items, and the first metadata may be associated with each of the plurality of content items. In addition, the at least one event detail may comprise a location and/or one or more participants.

In an embodiment, the method may obtain the event information from the virtual calendar automatically and periodically. Furthermore, the virtual calendar may be a third-party calendar application, and the method may obtain the event information from the third-party calendar application using an application programming interface.

In an embodiment, the method may comprise using the at least one hardware processor of the device to: receive audio information using a microphone of the device; convert the audio information into text; generate second metadata based on the text; and associate the second metadata with the one or more content items. The audio information may be received while the one or more content items are generated.

In an embodiment, the method may further comprise using the at least one hardware processor of the device to: detect an object in the one or more content items by matching one or more features of the one or more content items to a stored representation of the object; retrieve object metadata associated with the stored representation of the object; and associate the object metadata with the one or more content items. The step of matching one or more features of the one or more content items to a stored representation of the object may comprise: determining a geo-location of the device; and comparing a representation of the one or more features to a plurality of representations of objects associated with the determined geo-location. The object may comprise a face, a pet, and/or a landmark.

In an embodiment, the method may further comprise using the at least one hardware processor of the device to: receive biometric information from a user of the device; generate authorship metadata based on the biometric information; and associate the authorship metadata with the one or more content items.

In an additional embodiment, a non-transitory computer-readable medium having one or more sequences of instructions stored therein is disclosed. The one or more sequences of instructions, when executed by a processor of a device, cause the processor to: obtain event information from a virtual calendar, wherein the event information comprises at least one event detail and one or more parameters defining a time period; generate first metadata based on the at least one event detail; store the first metadata, in association with the time period, in a memory; and, subsequently, during the time period, retrieve the first metadata from the memory, and associate the first metadata with one or more content items generated on the device.

In an additional embodiment, a system for scheduling the association of metadata with content is disclosed. The system comprises: at least one hardware processor; a memory; and one or more software modules that, when executed by the at least one hardware processor, obtain event information from a virtual calendar, wherein the event information comprises at least one event detail and one or more parameters defining a time period, generate first metadata based on the at least one event detail; store the first metadata, in association with the time period, in the memory; and, subsequently, during the time period, retrieve the first metadata from the memory, and associate the first metadata with one or more content items generated by the system.

BRIEF DESCRIPTION OF THE DRAWINGS

The details of the present invention, both as to its structure and operation, may be gleaned in part by study of the accompanying drawings, in which like reference numerals refer to like parts, and in which:

FIGS. 20A and 20B illustrate an example process for tagging captured content with metadata, according to an embodiment;

DETAILED DESCRIPTION

In an embodiment, systems and methods are disclosed for adding descriptive metadata to content items, for example, to organize and facilitate searches for the content items once they are stored. As used herein, the terms "content," "content item," or "content items" may refer to any type of content, including, without limitation, images (e.g., photographs, collages, digital artwork, etc.), video recordings, audio recordings, animations, slideshows, electronic documents (e.g., spreadsheets, word-processing documents, PDF documents, etc.), etc. In embodiments, the addition of the descriptive metadata may be performed automatically or semi-automatically by a computing device, such as a smart phone, tablet, laptop, desktop, server, or other processing device.

After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. Process Overview

Embodiments of process(es) for adding descriptive metadata to content items will now be described in detail. It should be understood that the described process(es) may be embodied in one or more software modules that are executed by one or more hardware processors. The described process may implemented as instructions represented in source code, object code, and/or machine code. These instructions may be executed directly by the hardware processor(s), or alternatively, may be executed by a virtual machine operating between the object code and the hardware processors. In addition, the disclosed module(s) may be built upon or interfaced with one or more existing systems. Furthermore, the software modules may be integrated in a stand-alone application, an extension of another application, or integrated into an operating system. Alternatively, the process(es) may be embodied in hardware components, such as in an embedded system or integrated circuit (IC), or a combination of software and hardware components. Accordingly, as used herein, the term "module" should be interpreted as contemplating a software module, a hardware module, and a module comprising a combination of software and hardware. Furthermore, the term "module" or "modules," whether used in the singular or plural form should be interpreted as encompassing both a single module and, alternatively, a plurality of modules.

1.1. Metadata Generation Overview

Figure 1:
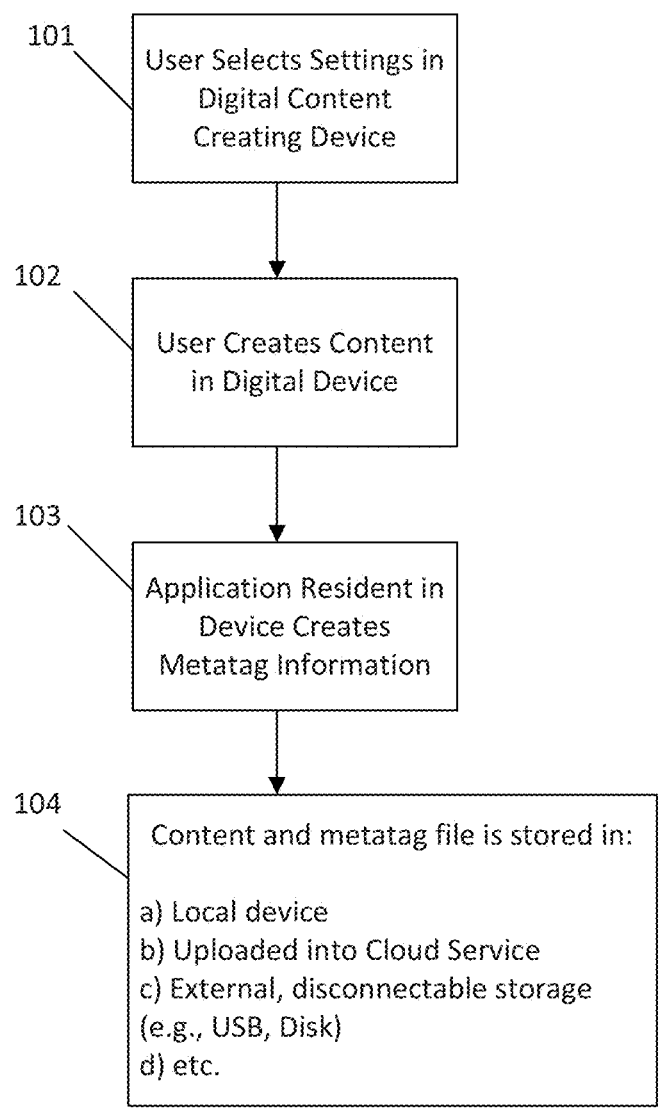
FIG. 1 illustrates a high-level flow diagram for a process of generating metadata for a content item, according to an embodiment.

FIG. 1 illustrates a high-level flow diagram for a process of generating metadata for a content item, according to an embodiment. In step 101, settings are received from a user at a digital device, such as a user device capable of capturing content (e.g., mobile phone, tablet, camera, scanner, etc.). These settings may comprise a selection of sources to be used to generate metadata, a specification of predefined metadata, a selection of user preferences, inputs for overriding defaults, and inputs for specifying other user-specifiable features. In step 102, a user may generate one or more items of content. For example, the user may use the device to capture content (e.g., taking a digital photograph or video using the camera in a smart phone, creating an electronic document using a word processor, etc.) or may transfer previously-captured content to the device (e.g., uploading a digital photograph to a server or cloud storage, transferring an image or video from external storage using a Universal Serial Bus (USB) or other connection type, etc.). In step 103, the device creates metadata (e.g., information to be associated with metatags provided for by a particular standard or file format), potentially according to one or more settings specified in step 101. In step 104, the device stores the generated metadata in association with the content. For example, the metadata (e.g., as a metatag file) may be embedded in the content file or stored as a separate sidecar file that is associated with the content file. The content and the associated metadata may be stored in the same location or separate locations, and may be stored locally on the device or stored remotely on another device (e.g., a server, cloud service, external storage, such as a flash drive, etc.). For example, the user may be provided with an option to upload the content with its associated metadata to cloud storage or another remote location over a network. Cloud storage can be particularly convenient, since such services are generally supported by staff, ensure data privacy, provide automated backup to prevent the loss of data, and/or provide failover to prevent the loss of access to data.

Figure 2:
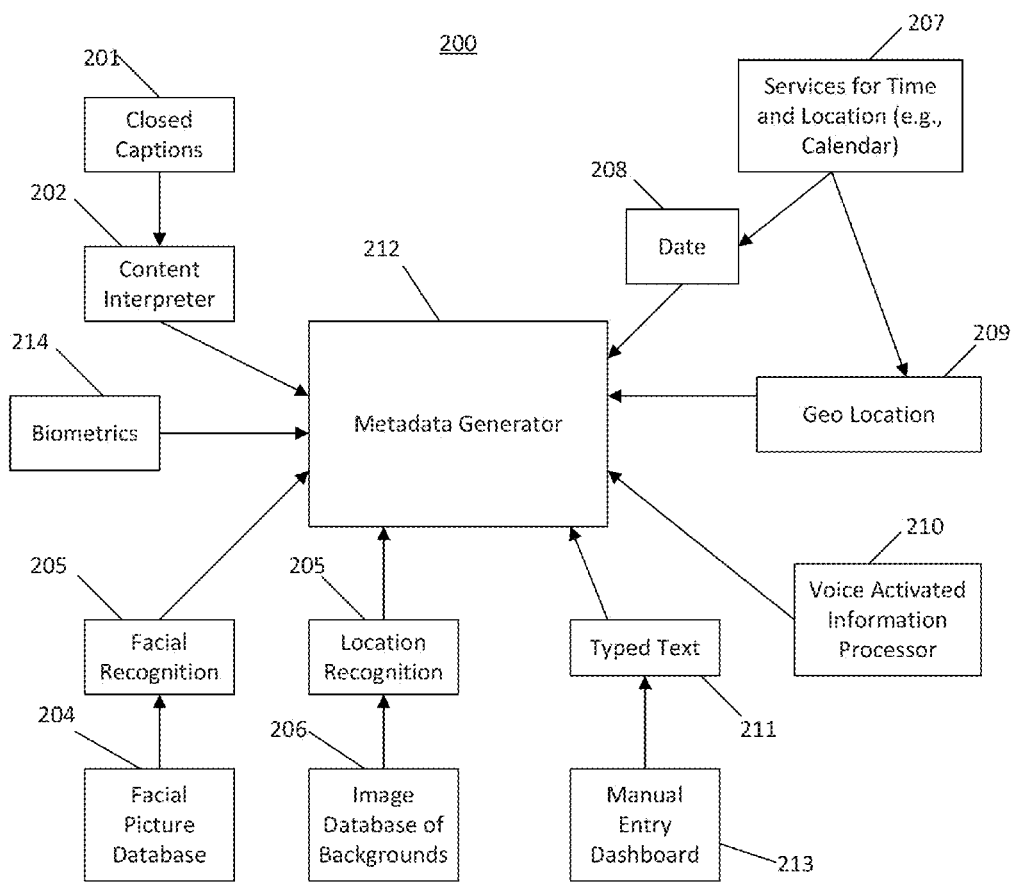
FIG. 2 illustrates various sources or inputs of information that can be used to generate metadata, according to embodiments.

FIG. 2 illustrates various inputs upon which metadata may be based, according to embodiments. Metadata generator 212 (which may be or be part of an application executing on a device) obtains information from one or more sources, generates metadata based on the obtained information, and associates the generated metadata with content (e.g., embedded in the content file or in a sidecar file). These sources may include, without limitation, closed captions 201 which may be processed by a content interpreter 202 (also referred to herein as a "closed-captioning module"), a facial-recognition database 204 which can be searched by a facial-recognition module 203 and/or an object-recognition database 206 which can be searched by an object-recognition module 205 and which may utilize geo-location information 209, scheduling or calendaring services 207 (also referred to herein as a "scheduling module") that associate a time period with locations, events, and the like (e.g., Microsoft Outlook™, Google Calendar™, Apple iCloud Calendar™, or other calendar applications, including a proprietary calendar application) and which may utilize date information 208 and/or geo-location information 209, geo-location information 209 which may be acquired from a GPS receiver, a voice information processor 210 (also referred to herein as an "audio module") which provides audio information, typed text 211 which can be manually input by a user via a dashboard user interface 213 provided by metadata generator 212, and/or biometrics 214.

As an example, geo-location information 209 can be automatically obtained (e.g., from a GPS receiver installed in the device that creates content) and associated with content at the time that the content is created. Thus, for example, as a user captures photographs while in Washington, D.C., the metadata generator 212 may acquire geo-location information, determine that the geo-location information corresponds to Washington, D.C. (e.g., by determining that the geo-location information is within the municipal boundaries of Washington, D.C.), and associate related metadata (e.g., the keywords "washington, d.c.," "washington," "district of columbia," etc.) to each of the photographs as they are captured.

Metadata generator 212 may execute in parallel with the creation of content with which the generated metadata is to be associated (e.g., automatically or semi-automatically in the background). Alternatively or additionally, metadata generator 212 may be executed before or after the creation of content to associate the generated metadata with content that will be created or content that has been previously created, respectively.

In embodiments or scenarios in which metadata generator 212 executes to generate metadata in parallel with the creation of content, metadata generator 212 may automatically (e.g., without any input from the user) or semi-automatically (e.g., prompting the user when needed, beneficial, and/or desired) execute in the background. For instance, metadata generator 212 may process content as it is captured—i.e., in real time or near-real time—to recognize faces or objects. As another example, metadata generator 212 may record audio and/or convert audio inputs into text (e.g., audio that is spoken by the user and/or captured during a video recording), in real time or near-real time, to be associated as metadata with the content being created. It should be understood that metadata for content may be generated from a single source or any combination of sources (e.g., serially or in parallel) described herein.

1.2. Content Sources Overview

Figure 3:
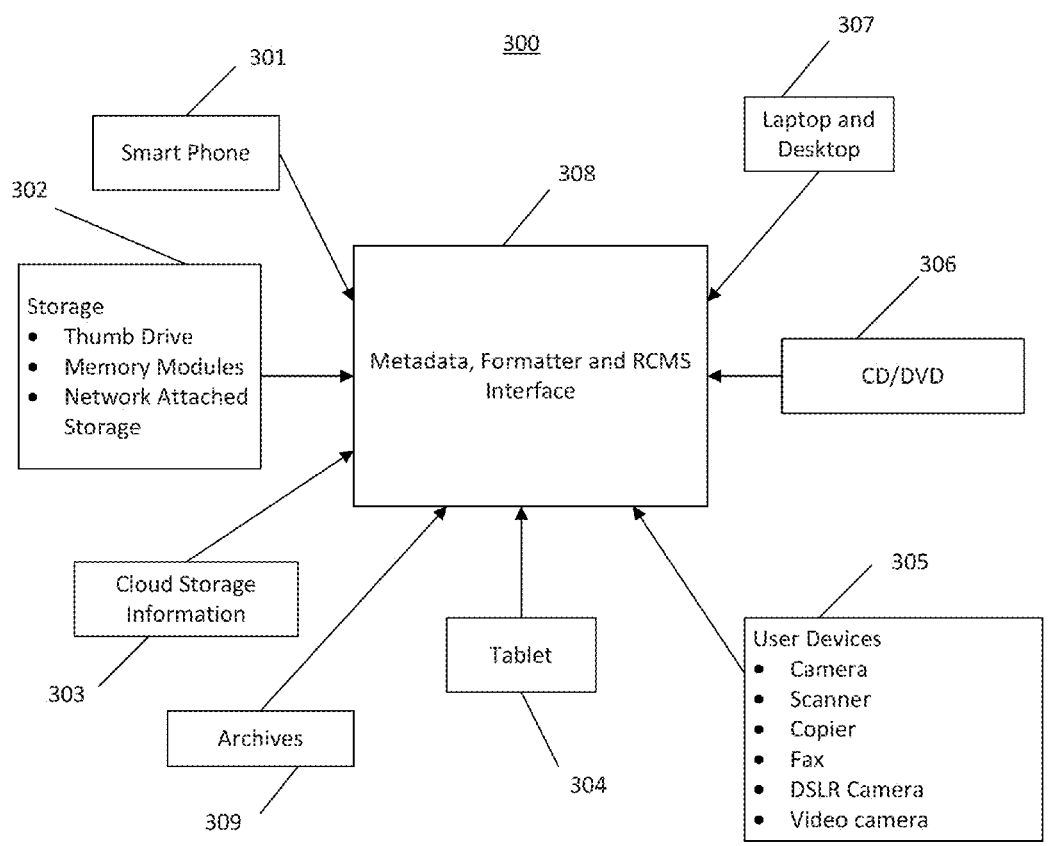
FIG. 3 illustrates various sources or storage locations of content items, according to embodiments.

FIG. 3 illustrates various sources or storage locations of content items, associated or to be associated with metadata (e.g., generated by metadata generator 212), which may be received or accessed by an interface 308 of a Relational Content Management System (RCMS), according to embodiments. An embodiment of the RCMS is disclosed in U.S. Provisional Patent App. No. 61/874,072, which is hereby incorporated herein by reference in its entirety. The RCMS may accept the content and associated metadata and prepare the data for the appropriate format or standard.

In an embodiment, the RCMS comprises an intelligent search engine that identifies content items which match one or more criteria, such as user-specified parameters and data associations. Whereas a conventional search engine performs searches for keyword matches and often returns unwanted information, the RCMS can return information based on more complex relationships between content items, e.g., determined using the unique metadata generated in the manners disclosed herein. In embodiments, the RCMS may also organize data for presentation to a user, e.g., in a hierarchical manner, using the unique metadata generated in the manners disclosed herein. The RCMS may be able to retrieve any accessible content in any format, and display the content on any user device. Thus, the RCMS leverages the metadata generated by the process(es) described herein to improve searching, sorting, and organization of content.

Smart phones 301 currently account for a substantial majority of the photographs and video content created today. Users of such devices can utilize the features discussed herein to tag, categorize, organize, sort, and search the content that they create, as well as the content created by others. The RCMS may also obtain content with metadata from storage devices 203, which may comprise thumb or flash drives, memory, internal or external hard disks, network-attached storage, and the like. Cloud storage 303 represents the storage of data in virtualized storage pools which are generally hosted by third-party data centers. In cloud storage, the data may be distributed across a plurality of hardware storage devices, which themselves may be geographically distributed. The RCMS provides a convenient interface for users to access, organize, and search content stored in the cloud. The RCMS may also provide an interface for archived content 309. Tablets 304, laptops and desktops 307, optical media 306 (e.g., Compact Discs (CDs) and Digital Video Discs (DVDs)) represent additional sources of content and metadata for the RCMS. In addition, the RCMS may pull content and metadata from other user devices 305 capable of generating content, such as cameras (consumer or professional devices), scanners, copiers, fax machines, Digital Single-Lens Reflex (DSLR) cameras, video cameras, etc. Essentially, the RCMS may receive or otherwise obtain content and metadata from virtually any type of device that is capable of generating or storing data.

1.3. Audio Metadata

In an embodiment, metadata generator 212 comprises an audio module (e.g., audio module 210) which enables the generation of metadata for content items using speech or other audio. In an embodiment, the audio module captures audio, which is then converted to text using a voice-to-text process, thereby allowing a user to associate textual metadata with a content item using his or her voice. Voice-to-text processes are well-known in the art, and thus, will not be discussed in detail herein. Alternatively or additionally, the captured audio may be stored as an audio file in the metadata associated with a content item. In either case, a user's speech may be captured by a microphone of a device that has been used, is being used, or will be used to generate content. This feature can be used to associate a narrative (e.g., story) with the content, identify the content, and/or provide other information to be associated as metadata with the content.

In an embodiment, the audio module allows a user to verbally specify technical or descriptive metadata before, during, or after creation of a content item. For example, the audio module may receive verbal input from a user while a content item is being generated (e.g., while a photograph is being captured or a video is being recorded). Additionally or alternatively, the audio module may acquire audio during the creation of a content item (e.g., the audio portion of a video being captured or, for a content item that is an audio recording, the audio recording itself), convert it to text, and then associate metadata, based on the text, with the content item. In either case, the audio module may execute in the background, while the content item is being captured.

In an embodiment, the audio module receives audio information, converts the audio information into text using a voice-to-text process, and automatically associates some or all of the text output from the voice-to-text process with a content item. For example, the audio module may parse the text output from the voice-to-text process to extract one or more character strings based on one or more criteria (e.g., proper names, words that appear relatively frequently, peculiar words that are not commonly used, words that are relevant to particular metatags for a standard file format, etc.). The audio module can then associate these extracted character strings—or, in embodiments, the entire text—with the content item as metadata (e.g., keywords which can facilitate subsequent organization of, sorting of, and searching for the content item).

In an embodiment, the audio module may parse the voice-to-text output and identify a command that causes certain metadata (e.g., previously-generated metadata or obtainable metadata), indicated by the command, to be associated with the content item that will be, is being, or has been created. For example, if the audio module identifies the command "GPS," the audio module may retrieve GPS coordinates from a GPS receiver of the device and associate the GPS coordinates, or geo-location information based on the GPS coordinates, with the content item. As another example, if the audio module identifies the command "recognize faces," the audio module may activate a facial-recognition process (e.g., embodied in facial-recognition module 203 or object-recognition module 205) to automatically detect and identify metadata for faces that appear in the content item, and associate the identified metadata (e.g., first and last name) with the content item.

Figure 4:
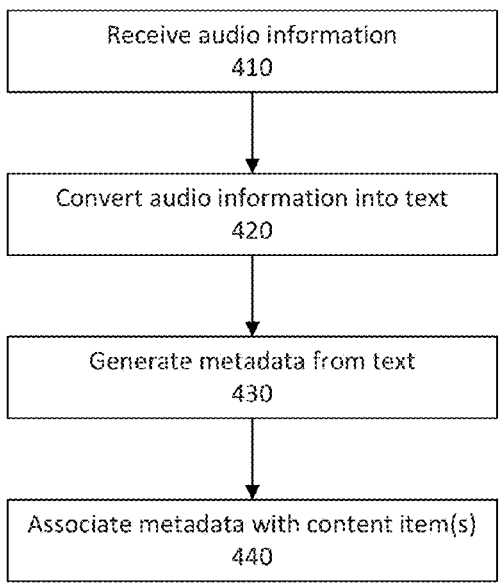
FIG. 4 illustrates a high-level flow diagram for an example process of associating verbally-received metadata with content items, according to an embodiment.

FIG. 4 illustrates a high-level flow diagram of a process 400 that may be implemented by the audio module. In step 410, audio information may be captured or otherwise received. As discussed above, the audio information may comprise verbal input from a user and/or an audio portion of a content item. In step 420, the received audio information is converted into text (e.g., using well-known audio-to-text processes). In step 430, metadata is generated from the text output from the conversion step. For example, the audio module may extract portions from the text to be used as metadata or may use the entire text output as metadata. In step 440, the metadata is then associated with the one or more content items.

1.4. Recognized Object Metadata

In an embodiment, metadata generator 212 comprises an object-recognition module (e.g., facial-recognition module 203 and/or object-recognition module 205) which enables the generation of metadata that identifies an object in a content item. For instance, the object-recognition module may determine a subject, such as a person or animal (e.g., pet), that is included in an image, video recording, and/or audio recording. This determination may be based on facial recognition, voice recognition, and/or the like. Additionally or alternatively, the object-recognition module may determine other objects, such as landmarks (e.g., buildings, monuments, geographical features, etc.), based on pattern recognition, current location of the device, and/or the like.

In an embodiment, the object-recognition module implements, or is interfaced with a module that implements, a facial-recognition process. The facial-recognition process may inspect a content item (e.g., image or video) and identify a subject (e.g., person or animal) of the content item. Specifically, the facial-recognition process may compare objects in the content item to a database of predefined representations of subjects (e.g., models or graphs of a subject's face) to determine whether any of the objects match a previously-learned face for a subject (e.g., persons of interest to the user, the user's pet, subjects appearing in previous content items generated by or stored for the user, etc.). For instance, there are relatively unique attributes of a face that can be parameterized for reliable matching, such as the vertical width of the forehead, vertical length of the nose, horizontal width of the lips, vertical distance between the lips and mouth, x-y positions and relationships between portions of the face (e.g., center of the eyes, eyebrows, ears, nose, etc.), etc.

In an embodiment, the object-recognition module implements a more general object-recognition process, in addition to, alternatively to, or comprising the facial-recognition process. The object-recognition process may inspect a content item and identify any object that is represented in a database of predefined representations of objects (e.g., people, animals, landmarks, etc.). It should be understood that the object-recognition process may identify objects in the same or a similar manner as the facial-recognition process. For instance, the object-recognition process may parameterize features and relationships between features in the content item, and then compare those parameters to the parameters of predefined representations of objects in the database to determine matches (e.g., using thresholds or confidence levels). Suitable techniques for object recognition, including facial recognition, are well-known in the art and will not be described in detail herein. It should be understood that, additionally or alternatively, voice recognition (also well-known in the art) could be implemented, in a similar manner, on audio, recorded during the generation of a content item (e.g., a video or audio recording) to automatically identify people or animals (e.g., pets) for whom audio (e.g., a voice, a bark, etc.) is acquired during the content generation process, and therefore, who are likely to appear either visually or vocally in the content item.

Objects, including face, pets, and/or sounds (e.g., voices), can be learned by the object-recognition module from previously-created content items. For instance, a user may manually tag or otherwise indicate an object in a previously-captured photograph or video, and associate the object with an identifier of the object. For example, in the case of facial recognition, a user may utilize a user interface (e.g., provided by the object-recognition module) to draw a rectangle around a face of a subject in a previously-captured photograph or video, and associate the tagged face with a name of the subject and/or other information. The object-recognition module may then generate a representation of the face (e.g., a graph or other model representing the features and relationships between features of the face), and store the "learned" representation of the face in a database in association with the specified name or other information. Then the object-recognition module may compare faces detected in subsequently-captured content items (e.g., photographs or videos) to the representation of the face in the database to determine whether or not they match. In the event that the object-recognition module determines that the face detected in a subsequently-captured content item matches the representation of the face in the database (e.g., within a certain threshold or tolerance representing a suitable confidence level), the module may generate metadata, comprising the associated name and/or other information, and associate the generated metadata with the subsequently-captured content item. It should be understood that objects, other than faces, can be identified in a similar manner. For instance, the object-recognition module may generate a representation of a pet, landmark, or sound (e.g., person's or pet's voice, Big Ben's chimes, mullah calls to prayer, street noise, or other noise indicative of a particular object, location, or type of object or location), based on a tag in a prior content item, to be used for pet, landmark, or sound recognition in subsequently-created content items and for the association of metadata related to the pet, landmark, or sound (e.g., a name of the pet or landmark, or a description of the sound such as the name of a landmark or other object recognized by its sound) with those subsequently-created content items. It should also be understood that the object-recognition module may detect a plurality of objects in a single content item, and associate metadata for each of the plurality of objects with the single content item.

In an embodiment, in order to reduce the processing burden of the object-recognition and/or facial-recognition process, the process(es) may limit the search to a certain geographical area, based on location data, at or around the time that the content item was created, for the user device that created the content item. For example, if a user captures an image of Mt. Rushmore using a device (e.g., smart phone), the object-recognition module may acquire geo-location information from the device (e.g., coordinate information from a GPS receiver), and limit its comparisons between objects in the captured image to representations of objects in the database that are located within a certain range from the location information for the device (e.g., within a certain radius from a point represented by GPS coordinates that identify the location of the device). In this case, the representations of objects in the database may comprise or be associated with (e.g., indexed by or based on) geo-location information (e.g., GPS coordinates) for the objects. Thus, in the example above, the object-recognition module may determine that one or more predefined representations of objects in the database are associated with location information within a certain distance from the user's device at the time that the photograph of Mt. Rushmore is or was captured, compare objects in the captured image to these one or more predefined representations of objects in the database (including a representation of Mt. Rushmore) to determine that an object in the captured image matches the representation of Mt. Rushmore (e.g., at a predefined confidence level), and retrieve or generate metadata associated with the predefined representation of Mt. Rushmore (e.g., the keyword "rushmore" or "mt. rushmore") to be associated with the captured image. Accordingly, at a later time, the user or another individual could type "rushmore" into a search engine for an image database that includes the captured photograph of Mt. Rushmore, and the search engine could search the metadata for the images in the image database and return the captured photograph as being relevant to the search.

In a similar manner, geo-location information can be used to facilitate facial recognition as well. For instance, the object-recognition module can be interfaced with an address book, extract address information for contacts of a user of a device from the address book, and limit searching of the predefined representations of faces in the database to faces belonging to individuals living within a certain distance from the current location of the user's device as determined from the extracted address information.

The database of predefined representations of objects may be a local database (e.g., stored on the user device which is executing metadata generator 212) or remote database (e.g., stored across a network on a server, in the cloud, etc.). Since the amount of information to be stored for a simple facial-recognition database of known subjects is relatively small, such a database could be stored locally. On the other hand, if the database included information for a large number of subjects (e.g., larger than the user's universe of known subjects) or also included information for numerous other objects, such as landmarks, the database would likely need to be stored remotely and accessed (e.g., queried) over a network (e.g., the Internet and/or a wireless communications network). However, in this case, it should be understood that portions of the remote database corresponding to a certain geographical location of the user device (e.g., landmarks within a certain distance from the user device) may be downloaded to a user device as a temporary local database for quicker access. The structure of the database can be in the form of a lookup table (e.g., a relational database).

In an embodiment, when an object is recognized (i.e., matched) in a content item, the object-recognition module may prompt the user to confirm that the object was properly recognized. For example, if an object in an image captured by a user is recognized as "Mt. Rushmore," the module may provide the user with a user interface comprising at least the portion of the image recognized as Mt. Rushmore, a prompt of "Is this Mt. Rushmore?" (or similar prompt), and one or more inputs for either confirming that the object is Mt. Rushmore or indicating that the object is not Mt. Rushmore. If the user confirms that the object was properly recognized, the object-recognition module may then generate appropriate metadata (e.g., the name of the object) to be associated with the content item.

Figure 5:
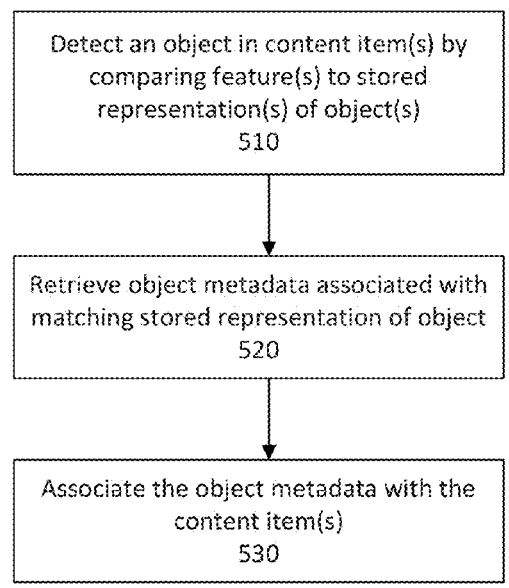
FIG. 5 illustrates a high-level flow diagram for an example process of associating metadata with content items based on object recognition, according to an embodiment.

FIG. 5 illustrates a high-level flow diagram of a process 500 that may be implemented by the object-recognition module. In step 510, an object is detected in one or more content items. As discussed above, this may be done by comparing graphical features in the content item with stored representation(s) of objects (e.g., in a local or remote database). In step 520, object metadata associated with the stored representation of the matching object is retrieved or generated. In step 530, the object metadata is then associated with the content item(s).

1.5. Scheduled Metadata

In an embodiment, metadata generator 212 comprises a scheduling module (e.g., scheduling module 207) which enables the generation of metadata for content items based on a virtual calendar or other scheduling mechanism. The module may determine a period of time or time window in which a particular set of metadata is automatically associated with any content items generated during that period of time. For instance, a photographer could generate and store metadata related to a future event (e.g., defined by a start and end date and time), and each photograph subsequently taken during that event may be automatically associated with the previously-generated and stored metadata. In an embodiment, this association of the previously generate and stored metadata with the photographs can be performed in the background, while photographs are being taken, such that the photographer may continue to focus on taking the photographs.

The period of time may be determined based on calendar information received for a user. For example, the scheduling module may comprise or be interfaced with a calendar module that provides a user with a user interface for entering scheduled events in his or her life, such as vacations, business travel, appointments, meetings, conferences, reminders, and the like. This calendar module may be a separate application (e.g., Google Calendar™, Microsoft Outlook™, etc.) and the scheduling module may communicate with the calendar module (e.g., by pulling information from the calendar module) via one or more application programming interfaces (APIs). Alternatively or additionally, the calendar module may be integrated with or be one in the same as the scheduling module or integrated into the metadata generator 212 along with the scheduling module. In either case, the scheduling module may parse the calendar information or extract information from specific fields (e.g., title, subject, date, location, participants, etc.) of the calendar information to be assigned to corresponding metadata fields of a content item.

In any case, the scheduling module may automatically or in response to a user interaction (e.g., with a user interface of the scheduling module) pull or otherwise extract scheduling or event information from the calendar module. The scheduling information may comprise event detail(s) and parameter(s) defining time period(s). The scheduling module may parse the scheduling information to identify the one or more time periods that are associated with scheduled event(s). The scheduling module may then determine appropriate metadata to be used during the identified time period(s) based on information extracted from the scheduling information about the schedule event(s) (e.g., event details parsed from the scheduling information or extracted from specific fields of the scheduling information). For example, if a user had specified, via the calendar module, that he would be having lunch with Jack and Jill at a restaurant named "The Hill" on Wednesday, Apr. 9, 2014, from 12:30 pm to 1:30 pm, the scheduling module may acquire this information from the calendar module, and extract the names "Jack," "Jill," and "The Hill" from the information. The scheduling module may store the time (e.g., timestamps representing a start time of Wednesday, Apr. 9, 2014, at 12:30 pm and an end time of Wednesday, Apr. 9, 2014, at 1:30 pm) in association with the names of the participants and the location. Subsequently, whenever a user creates content (e.g., using an application that comprises or is interfaced with the scheduling module), the scheduling module may determine whether the current time (e.g., a time maintained by a device on which the scheduling module is executing) matches any stored time periods, including the time period stored for Wednesday, Apr. 9, 2014, between 12:30 pm and 1:30 pm. Alternatively, the scheduling module may continuously monitor the current time and compare it to stored time periods while also monitoring whether content is being created (e.g., using an application that comprises or is interfaced with the scheduling module). In either case, any content created during a stored time period can be automatically associated with the metadata that is associated with that time period. For instance, in the illustrated example, any images captured on Wednesday, Apr. 9, 2014, between 12:30 pm and 1:30 pm, would be automatically associated with the descriptive metadata of "Jack," "Jill," and "The Hill." For example, if a photograph is taken during the time period, "Jack" and "Jill" may automatically be added to the metadata for the photograph (e.g., as subjects of the photograph, in the title or filename of the photograph, etc.) and "The Hill" may automatically be added to the metadata for the photograph (e.g., as the location at which the photograph was taken). In addition, the scheduling module could interface with the object-recognition module 205, discussed above, to limit searching by the facial-recognition process to participants extracted from the scheduling information and associated with the time period. For example, in the above example, based on the known participants determined from the scheduling information, the facial-recognition process could retrieve just the representations of faces for "Jack," "Jill," and the user from the database of learned faces, thereby increasing the speed and efficiency of the facial-recognition process.

Instead of or in addition to extracting scheduling information from a calendar module, the scheduling module may provide a user interface that allows a user to set a particular time period (e.g., a start date and end date) and specify particular metadata to be associated with content items created during that time period. For instance, the user interface may comprise inputs which allow the user to specify a start date and time and an end date and time, thereby defining a single or recurring time period, and a set of metadata to be associated with that time period (e.g., names of individuals, comments, title, location, etc.). After the user has specified a time period and metadata to be associated with the time period, the scheduling module may operate in the same manner as described above.

In an embodiment, the scheduling module can operate in conjunction with other modules and/or data, such as geo-location information 209 or object-recognition module 205, to detect discrepancies with scheduled metadata. For instance, if the scheduled metadata is extracted from an event occurring during a certain time period in a particular location, and the geo-location information indicates that the user is in a different location during that time period, the scheduling module can flag the discrepancy. In an embodiment, the scheduling module 207 may prompt the user when a discrepancy is detected. Furthermore, the scheduling module may request that the user confirm, modify, and/or cancel the scheduled metadata. As an example, if the extracted location of an event is in Japan and the geo-location information indicates that the user or user device is in New York when content is generated during the scheduled time period, the scheduling module may prompt the user with "Are you really in New York?" and/or provide a user interface with inputs that enable the user to modify the metadata or the user's calendar, confirm that the user is really in New York and cancel the association of the scheduled metadata with the generated content, deny that the user is really in New York and proceed with the association of the scheduled metadata with the generated content, etc. In a similar manner, if the scheduled metadata is extracted from an event for a certain time period in a certain location (e.g., New York), and the object-recognition module recognizes an object (e.g., Mt. Rushmore), known to reside at a different location, in a content item created during the time period, the scheduling module may similarly flag the discrepancy.

In an embodiment, the scheduling module can operate to associate scheduled metadata with content items after the content has been created and even if the content has been created using a different device than the device hosting the scheduling module. For example, when a content item is transferred to the device on which the scheduling module is executing and/or registered with an application comprising the scheduling module, the scheduling module may determine whether a creation time of the content item (e.g., as determined from a timestamp associated with the content item) is within a time period associated with scheduled metadata. If the creation time of the content item is within such a time period, the associated scheduled metadata may be automatically associated with the content item.

Figure 6:
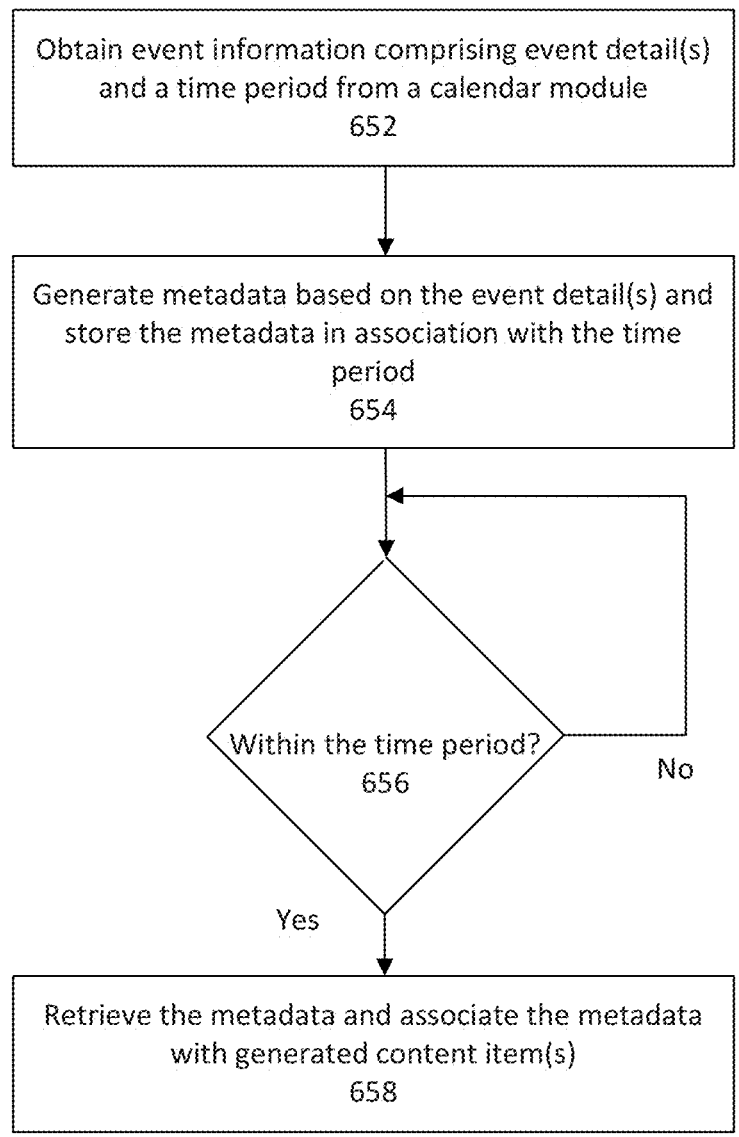
FIG. 6 illustrates a high-level flow diagram for an example process of scheduling metadata for association with content items, according to an embodiment.

FIG. 6 illustrates a high-level flow diagram of a process 650 that may be implemented by the scheduling module. In step 652, event information is obtained from a calendar module, such as a calendar application or the scheduling module itself. The event information may comprise one or more event details and one or more parameters that define a time period. In step 654, metadata is generated based on the event detail(s). The metadata may be stored in association with a representation of the time period defined in the event information. In step 656, it is determined whether the current time is within the time period defined in the event information. This may be determined in response to the generation of a content item, and may be performed each time that a content item is generated on a device on which the scheduling module is executing. For example, the scheduling module may be interfaced with, integrated with, or called by a content-generation module such that step 656 can be performed each time that new content items are generated. If the current time is not within the time period of interest, the scheduling module may block, sleep, end, etc. On the other hand, if the current time is within the time period of interest, in step 658, the metadata associated with that time period is retrieved and automatically or semi-automatically associated with the generated content item.

In an embodiment which utilizes process 650, an option may be provided to bypass one or more of the steps in process 650. For instance, a user may be provided with the option to turn off or otherwise bypass step 658. This option may be provided in the form of an input (e.g., icon, button, etc.) on a user interface, such as one or more of the user interfaces illustrated in FIGS. 12A-14B. The input may be a toggle input, which can be toggled by a user between an on state and an off state that correspond to an on state and an off state, respectively, of step 658. When the input (and thereby, step 658) is set to the on state, metadata associated with a current time period is retrieved and associated with the generated content item in step 658. In contrast, when the input (and thereby, step 658) is toggled to the off state, step 658 is not performed, such that the metadata associated with the current time period is not retrieved or, at least, not associated with the generated content item. In this manner, the user can easily turn off the association of preset event-related metadata to content items generated during a current time period that falls within a time period defined in the associated event information. For example, if, during an event represented by the event information, the user wishes to temporarily turn off step 658, he or she may do so by simply toggling or otherwise selecting the input. This may be useful, for instance, if the user wishes to capture a content item that is unrelated to the event for which the metadata was created, such as a photograph or video of an unexpected or intervening incident. In such a scenario, the metadata associated with the event may not be relevant to the intervening incident, and thus, it would not be appropriate to associate this preset event-related metadata with content item(s) captured during the intervening incident (e.g., an altercation occurring outside the window of a restaurant in which the user is having a lunch event). The input may be available and selectable before the content item is captured, during capture of the content item, after capture of the content item and before association of the preset metadata with the content item, after capture of the content item and after association of the preset metadata with the content item, or during any combination of these time periods, including during all of these time periods. In instances in which the input is toggled to an off state for a particular captured content item after the preset metadata has already been associated with the content item, the preset event-related metadata may be responsively disassociated with the content item. In addition, it should be understood that the state of the input and corresponding step 658 (i.e., on or off) may be persistent, such that step 658 remains in its current state for all subsequent content items until the user toggles step 658 to the other state via the input.

1.6. Authorship Metadata

In an embodiment, metadata generator 212 comprises an authorship module which enables the generation of metadata that identifies an author of a content item. The authorship module may acquire authorship information (e.g., an author's first and/or last name) from autobiographical information in a user's account (for embodiments which utilize user accounts) and/or from biometric information (for embodiments which utilize biometrics).

In an embodiment, the authorship module may acquire authorship information (e.g., first and last name) from an account associated with a user that is signed into an application (e.g., using credentials for an authentication process) embodying the authorship module or a device hosting the authorship module. Thus, the authorship module is able to retrieve the appropriate authorship information for the user that is presumably generating content at the time. It should be understood that the device may have accounts for a plurality of users, and thus, the authorship module may associate different authorship information with content depending on which user is signed in at the time that the content is generated.

In an embodiment, the authorship module may, alternatively or additionally, acquire authorship information from biometric information received at a device using one or more sensors or other devices capable of sensing biometric information (e.g., fingerprint reader, microphone, camera, accelerometer, etc.) and one or more processes capable of matching the received biometric information to known biometric information (e.g., voice recognition, face recognition, fingerprint recognition, etc.). Thus, a user could initially register his or her biometric information with the authorship module or device in association with a user account and/or user-specific metadata (e.g., first and last name). Then, a user could sign in to an application embodying the authorship module or the device using his or her biometric information, in which case the authorship module could acquire authorship information from a user account in the same manner as described above. Alternatively or additionally, an application embodying the authorship module could receive biometric information before, during, or after creation of a content item, match the received biometric information to the previously-registered biometric information, acquire the user-specific metadata associated with the matched, previously-registered metadata, and associate the user-specific metadata with content item.

As mentioned above, the authorship module may acquire authorship or other information from an account associated with a user that has signed in to the application using biometric information. In other words, the biometric information may be used as an authentication credential for the purpose of signing into the application. For example, the user may sign into the application by scanning his or her fingerprint using a fingerprint reader (e.g., integral to a mobile device executing the application). As long as the user's authenticated session is active, the authorship module may acquire information from the account as needed, and associate that information or other metadata derived from that information with captured content items. However, it should also be understood that, even in embodiments that do not derive metadata from the user's account, biometrics can still be used to authenticate the user for the purposes of signing in to the application.

Figure 7:
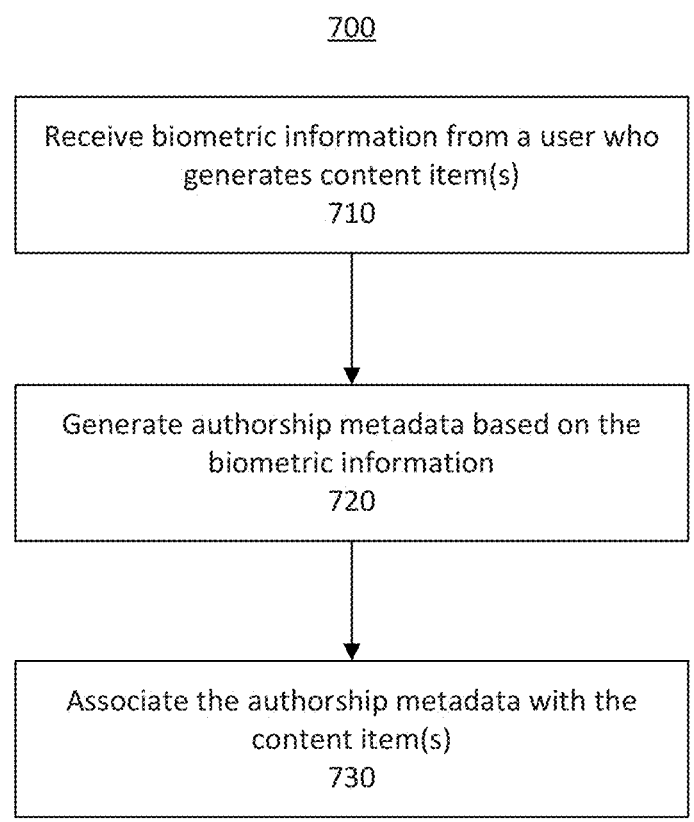
FIG. 7 illustrates a high-level flow diagram for an example process of associating metadata with content items based on biometric information, according to an embodiment.

FIG. 7 illustrates a high-level flow diagram of a process 700 that may be implemented by the authorship module. In step 710, biometric information is received from a user who generates content item(s). As discussed above, this biometric information may be received before, during, or after generation of the content item(s). In step 720, authorship metadata is generated based on the received biometric information. As discussed above, the authorship module may match the received biometric information to previously-registered biometric information in order to retrieve or generate the authorship metadata based on user-specific information associated with the previously-registered biometric information. In step 730, the retrieved or generated authorship metadata is then associated with the content item(s).

1.7. Closed-Captioning Metadata

In an embodiment, metadata generator 212 comprises a closed-captioning module (e.g., closed-captioning module 202) which enables the generation of metadata for content items based on closed captions 201 associated with the content items. Specifically, some video files comprise closed captions. Indeed, content, including content produced for the Internet, is increasingly becoming subject to government regulations that require closed captions. During the closed-captioning process (e.g., during live production or in post-production), the closed captions are embedded in or otherwise associated with the content as text information. Closed captions are generally produced for at least a significant amount, if not all, of the dialogue and sound effects present in the associated content.

The closed-captioning module may, automatically or in response to a user interaction, parse the text of the closed captions associated with a content item to extract one or more character strings based on one or more criteria (e.g., proper names, words that appear relatively frequently in the closed captions, peculiar words that are not commonly used, words that are relevant to particular metatags for a standard file format, etc.). The closed-captioning module can then associate these extracted character strings with the content item as metadata (e.g., keyword(s) which can facilitate subsequent organization of and searching for the content item).

In an embodiment, other modules can similarly generate metadata from elements, other than closed captions, which have been previously-associated with a content item. Specifically, the module(s) can parse a content item for embedded or otherwise-associated elements (e.g., other metadata) to identify or generate text based on the elements, and associate the text as metadata with the content item. In other words, new metadata can be derived from old metadata and associated with a content item (e.g., in addition to the old metadata).

1.8. Additional Types of Metadata

Additional types of metadata that may be generated or otherwise obtained and associated with content items will now be described, according to embodiments.

In an embodiment, a module may be provided that derives metadata based on GPS information. For example, the module may acquire GPS coordinates representing a current location of a user device. Based on the GPS coordinates, the module may determine an address (e.g., including street address, city, state, and/or Zip code) associated with the GPS coordinates (e.g., by querying a local or remote database using the GPS coordinates to retrieve an address associated with the GPS coordinates). This address may then be associated with content items captured by the user device while the user device is at the location represented by the GPS coordinates.

Additionally or alternatively, based on the GPS coordinates, the module may generate non-address metadata. For example, the module may allow a user to store GPS coordinates or other location data (e.g., an address) in association with particular metadata (e.g., in a local or remote database). Subsequently, whenever a content item is captured while the user device is at or within a predetermined range of the stored GPS coordinates or other location data, as determined by periodically or continuously acquiring GPS coordinates representing the user device's current location, the module may retrieve the metadata associated with the GPS coordinates or other location data. The retrieved metadata may then be automatically or semi-automatically (e.g., after confirmation from the user) associated with the captured content item.

As one illustrative, non-limiting example, while at home, a user may instruct the module (e.g., using one or more inputs) to acquire the current GPS coordinates for the user's device and associate these GPS coordinates with the user's home, for example, by inputting the text "Stephen's Home" in response to a prompt. In this case, the module stores the GPS coordinates, representing the user's home, with the metadata "Stephen's Home." Thus, whenever the user captures a content item (e.g., photograph or video) at or within a predetermined range of the stored GPS coordinates, the module may automatically or semi-automatically associate the metadata "Stephen's Home" with the content item. The predetermined range may be set to represent an area that approximates or encompasses the dimensions of a typical house or other building.

It should be understood that the user may associate multiple sets of GPS coordinates (or other location data) with metadata in this manner (e.g., for the user's office, the user's parents' home, the user's school, etc.). Furthermore, in an embodiment, if the user captures a content item at a current location, other than one at or within a predetermined range of any stored location data, the module may automatically prompt the user to enter metadata (e.g., a name) for the current location. The module may also automatically store the current location in association with the entered metadata, such that it may be subsequently retrieved and associated with future content items created at or within a predetermined range of that location.

In an embodiment, a module may be provided that derives metadata from one or more contacts of a user. For example, the module may comprise, be integrated in, or interface with an electronic rolodex of the user (e.g., an address book application or other application that comprises contact information). The module may extract or derive metadata from this contact information.

As one illustrative, non-limiting example, the module may acquire an address or other location data of one or more contacts from the contact information, and compare the address or other location data to a current location of the user device. In a specific embodiment, the module may acquire GPS coordinates representing a current location of the user device, retrieve an address associated with the acquired GPS coordinates (e.g., in a similar or identical manner as discussed above), and compare the retrieved address with addresses in the contact information. If the retrieved address matches an address in the contact information, the module may generate metadata based on the corresponding contact information and automatically or semi-automatically associate the generated metadata with any content items captured at or within a predetermined range of the current location of the user device. For example, if the current address matches an address for a contact named "John Doe," the module may extract the contact's name and generate metadata comprising the text "John Doe's Home." Accordingly, a photograph or video captured at that location by the user device may be automatically or semi-automatically associated with the metadata "John Doe's Home." It should be understood that the matching of a current location of the user device to a location associated with a contact in the contact information may be performed by different means than those described herein (e.g., by matching current GPS coordinates to GPS coordinates stored for contacts in the contact information, etc.).

2. Example Application

An example software application that embodies one or more of the modules, processes, methods, functions, etc., discussed herein, and which may comprise or implement metadata generator 212 and its associated modules (e.g., the audio module, object-recognition or facial-recognition modules, scheduling module, authorship module, and/or closed-captioning module, described elsewhere herein), will now be described according to an embodiment.

2.1. Overview

Figure 8:
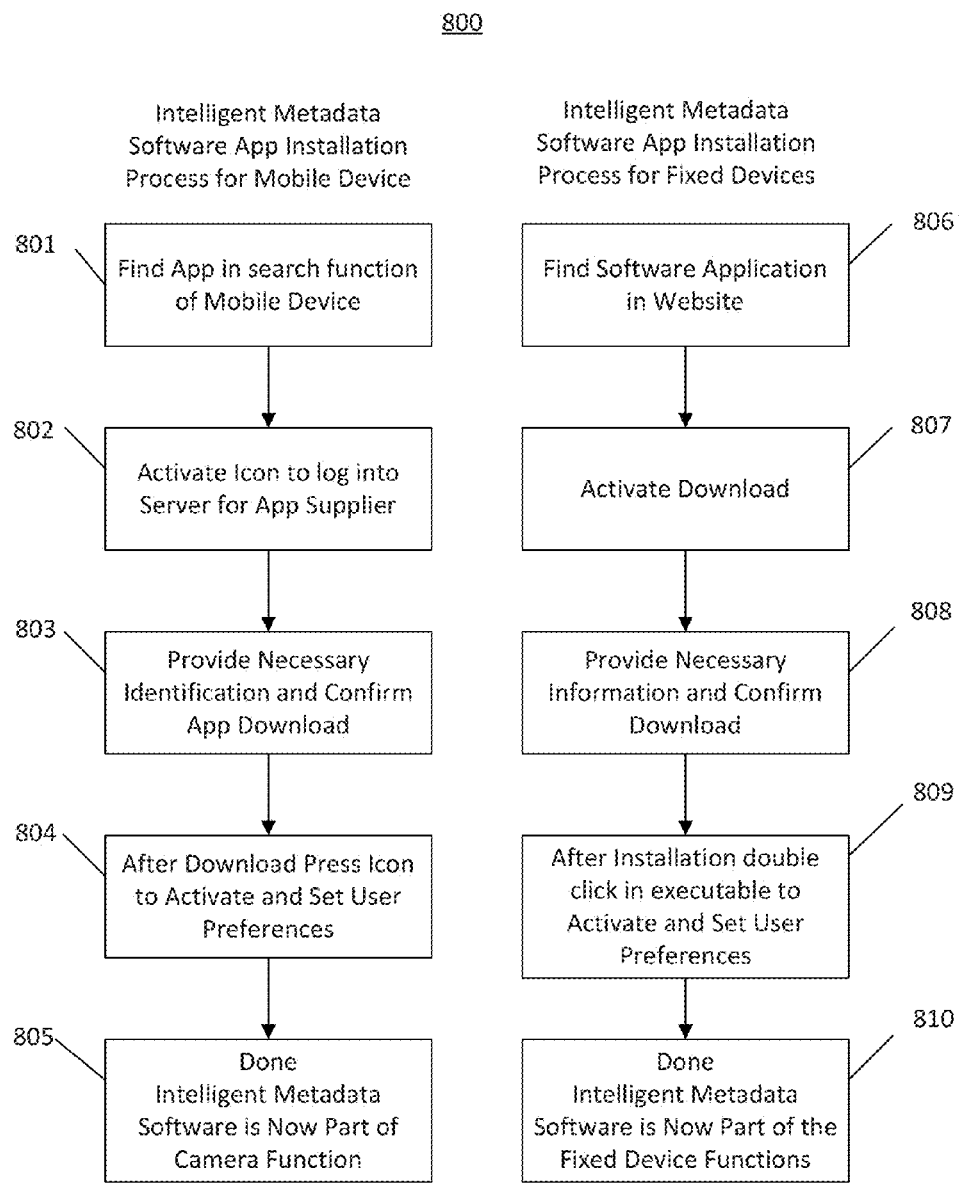
FIGS. 8A-8B illustrate high-level flow diagrams for processes of installing a software application on a device, according to embodiments.

FIGS. 8A-8B illustrate high-level flow diagram for processes 800 for installing a software application that implements one or more of any of the various modules, processes, methods, functions, etc., described herein. FIG. 8A illustrates a process for installing the application on a mobile device, such as a smart phone. In step 801, a user may query an "app store" or other application provider to locate the application. In step 802, the user may initiate a download of the application to the user's device. In step 803, the user may need to supply identification information (e.g., credentials such as a username and password) and confirm download (and, optionally, purchase) and/or installation of the application on the user's device. Installation may comprise integrating or interfacing the application with a camera function of the device. In step 804, the user may activate the installed application and specify settings (e.g., information used to generate metadata such as authorship or device information, user preferences, overriding of defaults, authentication credentials, other identifying credentials if the application is to be used by multiple users, etc.) for the application. In step 805, the process is complete.

FIG. 8B illustrates a process for installing the application on a non-mobile or fixed device, such as a desktop computer, workstation, or server. In step 806, the application is located either on a website or computer-readable storage medium, such as a CD, DVD, external drive, etc. If the application is located on a website, in step 807, the application is downloaded. In addition, in step 808, the user may need to supply identification information and confirm download and/or purchase of the application. In step 808, the user may also initiate installation of the application, whether downloaded from a website or accessed from a computer-readable storage medium. Once the application has been installed, in step 809, the user may activate the installed application and specify settings for the application. In step 810, the process is complete.

While the application is primarily discussed as a stand-alone client, it should be understood that other implementations are possible. For example, in an embodiment, the application may be implemented as a web application that runs in a web browser or is created in a browser-supported programming language, such as JavaScript, Hypertext Markup Language (HTML), and/or CSS. In such an embodiment, the web browser may act as a thin client that enables the application (e.g., by rendering the user interfaces of the application).

The application, whether installed on a mobile or fixed device, may provide a dashboard user interface comprising inputs (e.g., text-input fields, icons, checkboxes, buttons, drop-down menus, screen commands, etc.) representing tools that can be used to create and/or modify metadata, create and/or modify content items, access or use features of the RCMS (e.g., organizing content items, searching content items, sorting content items, etc.), and/or the like. The dashboard user interface may also comprise additional tools. For example, in the case of a workstation for a film or broadcasting professional, the dashboard user interface may be customized to incorporate tools that are applicable to that industry.

In an embodiment, the application may populate metadata fields of content items using an automatic mode or manual mode. Manual population may comprise user input of descriptions, keywords, ratings, event information, captions, voice comments that are converted to text, confirmations of automatically generated metadata, and the like. Automated population of metadata fields may utilize scheduling, object recognition, including facial recognition, geo-location information, date, time, and the like. For instance, the application may acquire representations of objects (e.g., faces) and/or other information, store the information in a local or remote database, and subsequently use the acquired and stored information in conjunction with object-recognition software, voice-recognition software, and/or geo-location information (e.g., GPS coordinates) so that content items (e.g., photographs, video, audio recordings, etc.) can be automatically associated with metadata comprising the name of a person, object, location, etc. in the content item. As another example, the application may store predefined metadata (e.g., event details obtained from a user's calendar) in association with a time period, and associate any content generated during that time period with the predefined metadata. In addition, the application may automatically populate content items with metadata, such as a title, subject, tags, ratings, keywords, captions, event information, comments, authorship, filename, storage location, etc. In any case in which a content item is automatically associated with metadata, the application may prompt a user (e.g., via one or more user interfaces) to confirm and/or deny that the metadata is correct and/or should be associated with the content item prior to associating the metadata with the content item. Alternatively or additionally, the application may also allow the user to modify the metadata prior to associating the metadata with the content item.

In an embodiment, the application may utilize metadata templates for automatically populating content items with metadata. For example, the application may generate metadata, retrieve a metadata template applicable to a particular content item and/or file format, populate the retrieved metadata template with the generated metadata, and associate the populated metadata template with the content item. The metadata templates may comprise fields corresponding to particular types of metadata (e.g., location metadata, name metadata, etc.). Advantageously, in an embodiment, the application also allows a user to populate multiple content items with metadata in bulk (e.g., using the discussed metadata template(s)), as well as populate individual content items with metadata.

Figure 9:
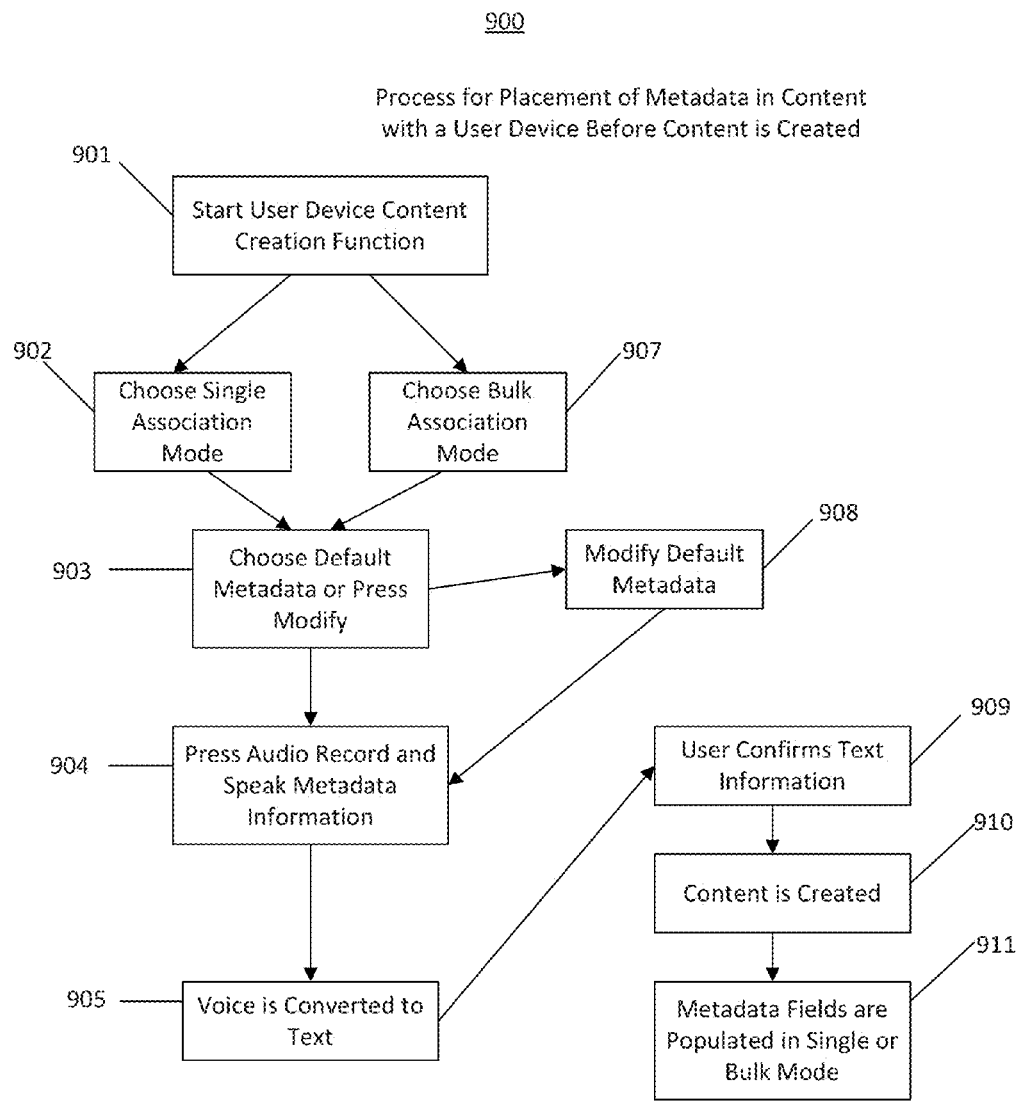
FIG. 9 illustrates a high-level flow diagram for an example process of using the application for adding metadata to content items in a device that is capable of generating content, according to an embodiment.

FIG. 9 illustrates a high-level flow diagram for an example process 900 of using the application for adding metadata to content items in a device that is capable of generating content, according to an embodiment. In step 901, the user of the device initiates execution of a content creation function in the device (e.g., a camera). The user may be prompted or otherwise choose whether content files created during the content creation process 900 should be associated with metadata and/or named individually or in bulk. For instance, if the user intends to capture multiple content items in quick succession (e.g., capturing multiple photographs using a fast shutter), the user may choose to associate all of such content items with bulk metadata in step 907. Otherwise, the user may choose to specify metadata (or a filename or prefix) for each individual content item (e.g., only the next captured photograph) in step 902.

In step 903, the user may be prompted to choose or modify default or other previously-provided metadata (e.g., provided as user settings in step 804 or 809 of processes 800) and/or types of metadata. If the user chooses to modify the previously-provided metadata and/or metadata types, then, in step 908, the user may modify the previously-provided metadata and/or metadata types. For example, in step 903, the user may select one or more metadata types, such as geo-location information, author information, etc., to be automatically added to the created content.

In step 904, the user may record audio data, for example, by selecting an audio record button or icon in a user interface of the application. This may initiate the audio module 210 discussed elsewhere herein, which may provide a visual or audio prompt to indicate that sound is being recorded (e.g., via a microphone of the device on which the application is installed). The user may then verbally input a filename or metadata, such as a description of (e.g., narrative, story, etc.), comment about, or keywords for the content that is being created. In step 905, the audio may be converted to text, either after the audio recording has been completed and/or in real time as the audio is being captured. This conversion may utilize well-known voice-to-text processes. In step 909, the text may be displayed on a display of the user device after the audio recording has been completed and/or in real time as the audio is being captured. Thus, the user may confirm that the text output from the voice-to-text process accurately represents the audio. The user may also be provided with one or more inputs for modifying the text prior to confirming it. In a similar manner, other metadata that is generated (e.g., the outputs of object-recognition or facial-recognition processes, geo-location information, etc.) may also be displayed to the user for confirmation and/or modification.

In step 910, the content is created, and, in step 911, the generated metadata is associated with the created content. For example, the metadata generated by metadata generator 212 may be embedded in the content file or associated with the content file (e.g., in a sidecar file). This may be performed after each individual content file has been created or in bulk after a plurality of content files have been created, depending on which option was specified by the user in step 902 or 907.

Figure 10:
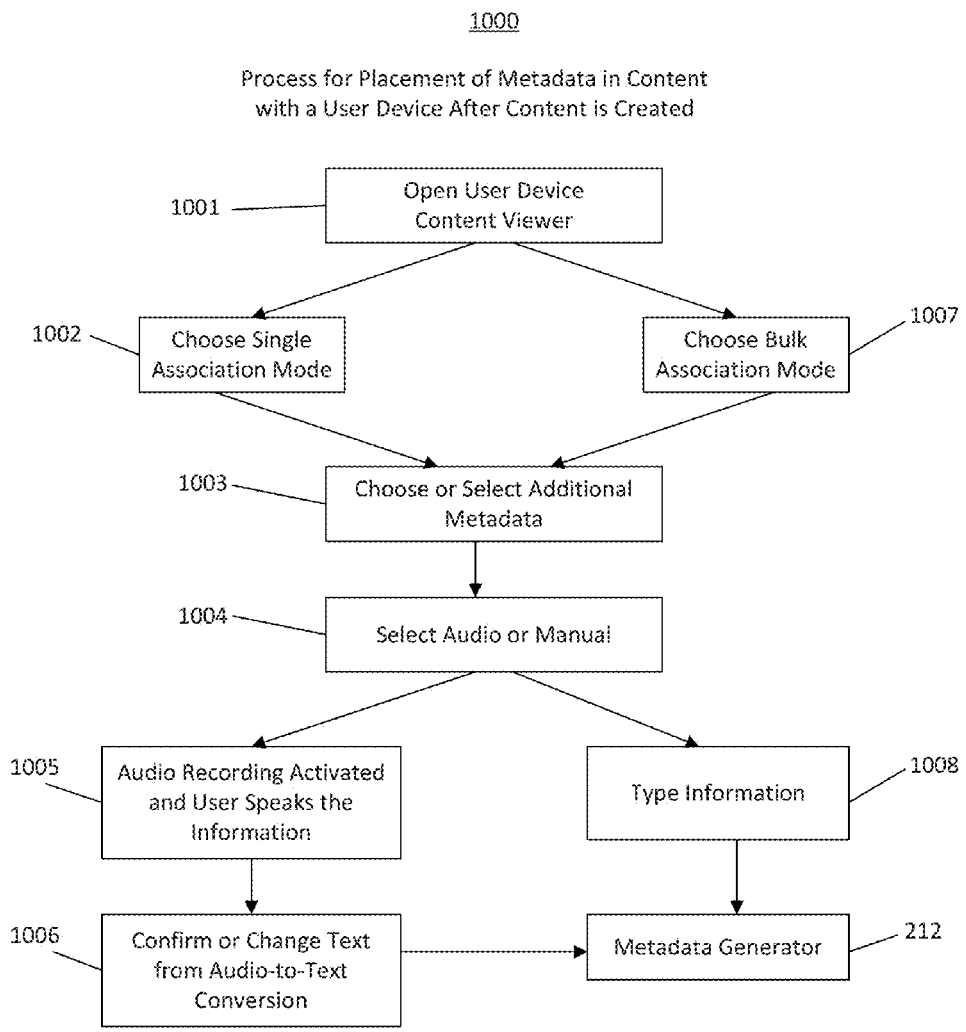
FIG. 10 illustrates a high-level flow diagram for an example process of using the application for adding metadata to content items, according to an embodiment.

FIG. 10 illustrates a high-level flow diagram for another example process 1000 of using the application for adding metadata to content items, according to an embodiment. Whereas FIG. 9 illustrates a process 900 of generating metadata during the creation of a content item, FIG. 10 illustrates a process 1000 of generating metadata after the creation of a content item on a device that may or may not have generated the content item. In step 1001, a user opens, on the device, a content viewer for viewing or selecting one or more content items. The user may be prompted or otherwise choose whether content files viewed or selected during the process 1000 should be associated with metadata and/or named individually or in bulk. For instance, if the user intends to assign the same metadata to multiple content items, the user may choose to associate all of such content items with bulk metadata in step 1007. Otherwise, the user may choose to specify metadata (or a filename or prefix) for each individual content item in step 1002.

In step 1003, the user may be prompted or otherwise be provided with the ability to select or specify metadata (or a filename or prefix to be used for naming content items) and/or metadata types. For example, in step 1003, the user may select one or more metadata types, such as geo-location information, author information, etc., to be added to the selected content item(s).

In step 1004, the user may also provide an audio or text input to be added as metadata to the selected content item(s). If the user chooses to provide audio input, in step 1005, audio module 210 may be activated and an audio recording may be captured, converted to text, and, in step 1006, confirmed and/or modified by the user. Steps 1005 and 1006 of process 1000 may be identical or similar to steps 904, 905, and 909 of process 900. On the other hand, if the user chooses to enter text manually, in step 1008, text input may be received from the user via one or more input devices (e.g., virtual keyboard, hardware keyboard, touch panel, pointing device, etc.). Whether input verbally or manually, the text may be provided to metadata generator 212 to be converted into metadata that is then associated with the selected content item(s).

2.2. Example User Interfaces

Example user interfaces for the example software application will now be described according to an embodiment for use in a mobile device, such as a smart phone. These user interfaces, collectively, may implement the dashboard discussed elsewhere herein.

Figure 11A:
FIGS. 11A-11C illustrate example user interfaces for activating an application that associates metadata with content items, according to an embodiment.
Figure 11B:
Figure 11C:

When the application is initiated (e.g., by selecting an icon), a splash screen, such as the one illustrated in FIG. 11A, may be temporarily displayed while the application is loaded. Once the application has been sufficiently loaded, the application may replace the splash screen with a sign-in screen, such as the one shown in FIG. 11B. As shown, the sign-in screen may comprise inputs for submitting authentication credentials (e.g., a username and password) for an existing account, as well as an input (e.g., link) for creating a new account. In scenarios in which multiple users may have access to the mobile device, authentication can be used to identify an author of content that is created using the application. Specifically, the authentication credentials may be associated with a name of the user (e.g., first name and last name), which can be automatically added as authorship metadata to content created using the application during the time that the user is signed in to the application. Authentication may also be used to restrict access to local and/or remote resources. For instance, the application may provide access to user-specific data—such as a content gallery (e.g., listings of content created or stored by the user), user information (e.g., personal information, payment information, etc.), and the like—that is stored in a local database (i.e., on the device) and/or in a remote database (e.g., on a server or in cloud storage). If a user chooses to create a new account, the application may display a user interface for inputting registration information (e.g., first name, last name, email address which may be used as a username or a separate username, password, etc.), such as the one shown in FIG. 11C. After the user submits the registration information, the application can create a new account, comprising the registration information, for the user in a local and/or remote database.

Figure 12A:
FIGS. 12A-12B illustrate example user interfaces for navigating an application that associates metadata with content items, according to an embodiment.
Figure 12B:
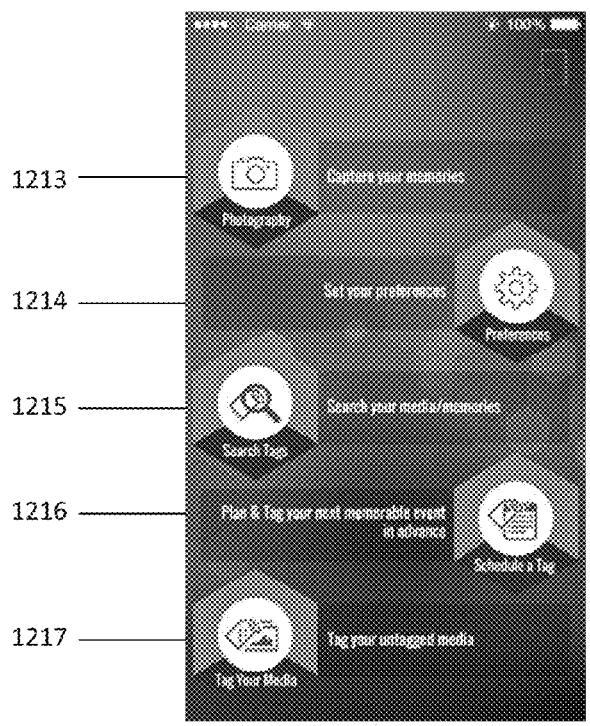

FIG. 12A illustrates a user interface that is displayed by the application after a user signs in to the application, according to an embodiment. As shown, the user interface comprises inputs for capturing a photograph or video as well as an image currently being received by a camera of the device. The user interface also comprises an input 1202 (e.g., icon), which if selected causes the application to display a menu, such as the menu shown in FIG. 12B. The menu allows a user to navigate between the various features of the application. As shown in FIG. 12B, the menu may comprise input 1213 which directs the user to user interface(s) for capturing content items (e.g., as illustrated in FIG. 12A and FIGS. 13A-13R), an input 1214 which directs the user to user interface(s) for setting user preferences (e.g., as illustrated in FIGS. 14A-14B), an input 1215 which directs the user to user interface(s) for searching content stored for the user (e.g., as implemented by the RCMS and/or illustrated in FIGS. 15A-15B), an input 1216 which directs the user to user interface(s) for scheduling metadata (e.g., as implemented by the scheduling module 207 and/or illustrated in FIGS. 16A-16B), and/or an input 1217 which directs the user to user interface(s) for tagging previously-created content (e.g., as illustrated in FIGS. 17A-17C).

Figure 13A:
FIGS. 13A-13R illustrate example user interfaces for associating metadata with generated content items, according to an embodiment.
Figure 13B:
Figure 14A:
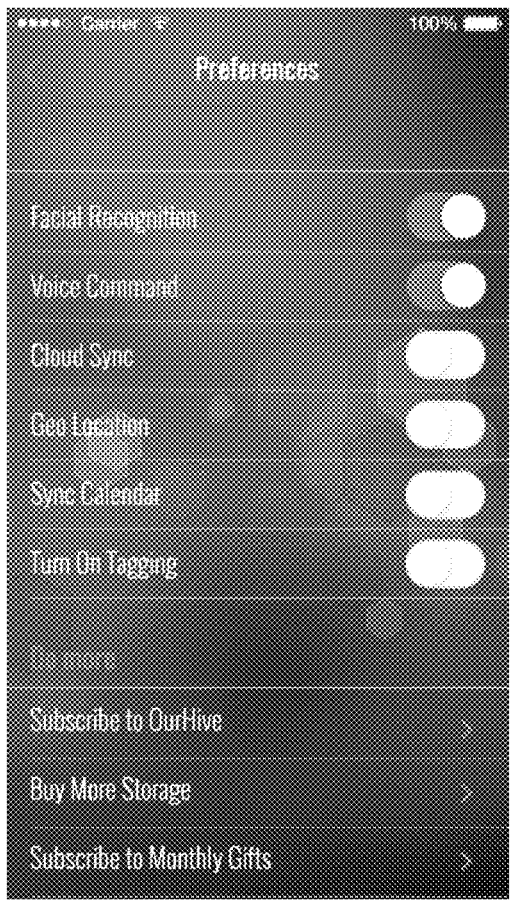
FIGS. 14A-14B illustrate example user interfaces for setting user preferences for an application that associates metadata with content items, according to an embodiment.
Figure 14B:
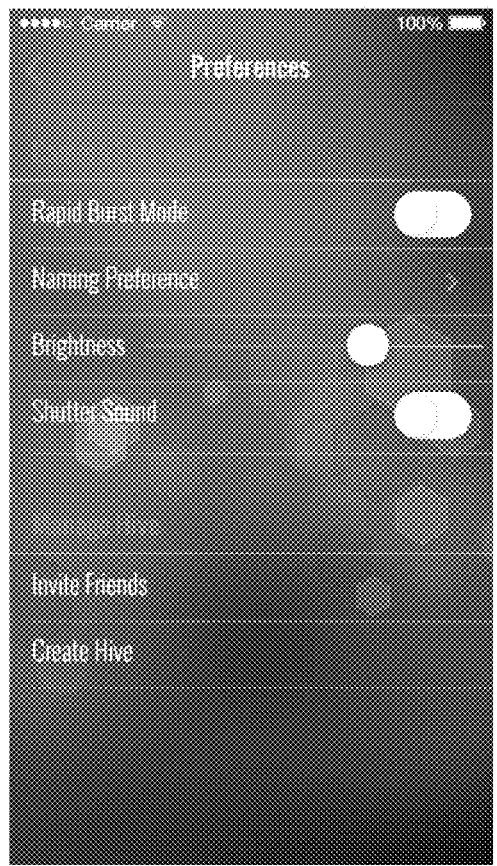

If a user selects input 1213, the application may direct the user to the user interfaces in FIGS. 13A-13R, which illustrate user interfaces for capturing content and associating the content with metadata. FIG. 13A illustrates a user interface for capturing an image or video in portrait mode, whereas FIG. 13B illustrates the user interface for capturing an image or video in landscape mode. As is well-known in the art, the user interface may be switched between the portrait and landscape modes based on the orientation in which the user device is held, as may be determined based on one or more sensors (e.g., accelerometers) within the device. The user interface may comprise inputs (e.g., selectable icons) for capturing an image, capturing a video, viewing the last captured image or video, turning a flash on or off, turning a microphone on or off or using a microphone to capture verbally-input metadata, switching the camera being used between a front-facing camera and rear-facing camera of the device, and/or the like.

Figure 13C:
Figure 13D:

FIGS. 13C and 13D illustrate the user interface of FIGS. 13A and 13B being utilized to capture video. If a user selects the icon for recording a video in the user interface of FIG. 13C, the application may begin recording video frames using a camera of the device and display a recording user interface, as shown in FIG. 13D. The recording user interface may indicate the length of the current recording and comprise inputs for changing a zoom amount of the camera, pausing the recording, stopping the recording, and/or the like. Once a user stops the video recording, the application may direct the user to user interfaces for receiving and/or confirming metadata that should be associated with the recorded video.

Figure 13E:
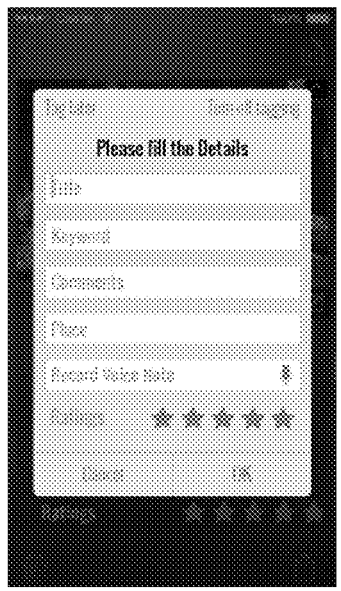
Figure 13F:
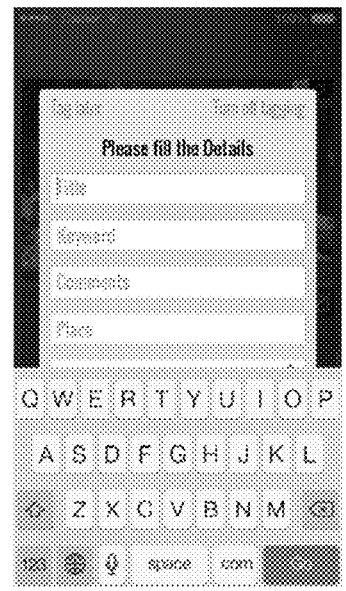

Once a content item is generated (e.g., an image or video captured using the user interfaces shown in FIGS. 13A-13D), the application may provide the user with user interface(s) for specifying and/or confirming metadata to be associated with the generated content item, as illustrated in FIGS. 13E-13P. FIG. 13E illustrates a user interface comprising inputs for manually entering metadata and/or confirming predefined or scheduled metadata. Inputs may be provided for a user to set a title, keyword(s), comments, location information, and a rating for the content, as well as to record an audio note to be associated with the content item. As a user selects text input fields, a virtual keyboard may be displayed for entering characters into the input fields, as illustrated in FIG. 13F. In some embodiments, a selectable range of rating inputs may be provided so that the user can rate the content item (e.g., on a scale of one to five by selecting one of five star-shaped inputs).

Figure 13G:
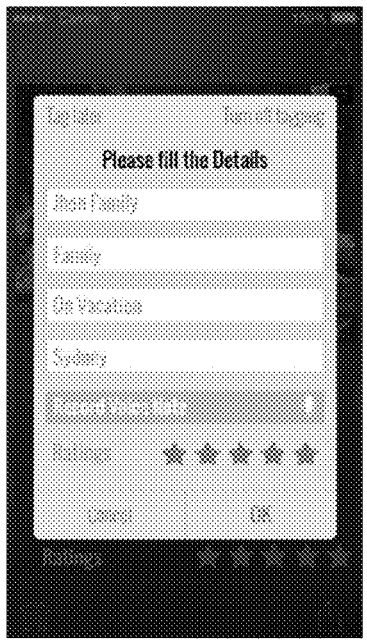
Figure 13H:
Figure 13I:
Figure 13J:
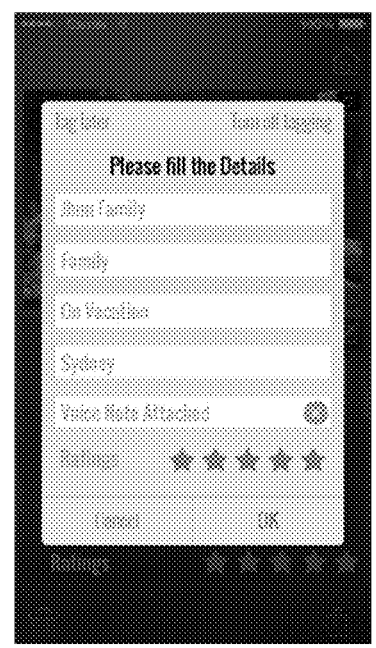
Figure 13K:

As illustrated in FIG. 13G, a user may also select an input for recoding an audio note. Once such an input is selected, the application may display a user interface that prompts the user to speak and comprises an input for ending the audio note, as illustrated in FIG. 13H. Once a user has completed recording of an audio note, the application may display a user interface with inputs for playing the audio note and re-recording the audio note, as illustrated in FIG. 13I. In embodiments which automatically convert such audio notes to text (e.g., using audio module 210), the user interface may alternatively or additionally comprise inputs for confirming and/or modifying a voice-to-text output. As illustrated in FIG. 13J, after a user has recorded an audio note, the audio note may be attached to the metadata. As illustrated in FIG. 13K, the metadata for the created content item may be displayed to the user in a user interface. The user interface may comprise an input for editing the metadata, which, if selected, may return the user to the user interface in FIG. 13J for editing the metadata.

Figure 13L:
Figure 13M:

FIGS. 13L-13P illustrate user interfaces for tagging faces in a content item with metadata, such as, the name of the person corresponding to each face that is tagged. As illustrated in FIG. 13L, a user may tag a face or select a face that the application has automatically tagged (e.g., using image processing algorithms that analyze images and detect human faces in the images) in a content item, and manually enter a name or other metadata to be associated with the face using a virtual keyboard that is activated upon the selection. Then, as illustrated in FIG. 13M, the names (or other metadata) may be overlaid over the content item (e.g., in a "text bubble") at a position that corresponds to the associated face to indicate that the face is associated with metadata and to specify the metadata with which the face is associated.

Figure 13N:

Additionally or alternatively, as illustrated in FIG. 13N, a user may tag a face or select a face that the application has automatically tagged in a content item, and verbally input a name or other metadata to be associated with the face using a similar method as described above, with respect to FIGS. 13H and 13I, for creating an audio note. For instance, when the user selects the face or tag, the application may display a user interface that prompts the user to speak and comprises an input for ending the verbal input and viewing a voice-to-text output for the verbal input. As illustrated in FIG. 13O, once a user speaks the metadata (e.g., the name "Daisy"), the application (e.g., audio module 210) may convert the user's speech into text and display the text along with inputs for editing the text and confirming the text. Once the text has been confirmed by the user, the text may be associated as metadata with the tagged face of the content item. Then, as illustrated in FIG. 13P (which is identical or similar to the user interface illustrated in FIG. 13M), the names (or other metadata) may be overlaid over the content item (e.g., in a text bubble) at a position that corresponds to the associated face to indicate that the face is associated with metadata and to specify the metadata with which the face is associated.

While FIGS. 13L-13P have been described in the context of tagging faces and associating the faces with metadata, it should be understood that the same user interfaces and methods may be used to tag other types of objects and associating those objects with metadata. Besides faces, such objects may comprise animals (e.g., pets), landmarks, vehicles, buildings, and any other object that is capable of being identified in an image or video. For example, a user may tag the object or select an object that the application has automatically tagged in a content item, and manually or verbally input a name or other metadata to be associated with the object using the methods described above with respect to FIGS. 13L-13P. It should also be understood that similar methods may be used to tag audio segments in an audio recording (e.g., by associating a segment of audio corresponding to a person's voice with the name or other metadata related to the person and/or content of the audio segment).

FIGS. 13Q and 13R illustrate user interfaces for sharing or otherwise utilizing a content item. As illustrated in FIG. 13Q, the application may provide the user with a user interface for selecting one of a plurality of options for using the content item. For example, the user interface may comprise inputs which enable the user to share the content item (e.g., on a social networking site or application), store the content item in a remote database (e.g., on a server or in cloud storage), and/or create a gift or other item using the content item (e.g., a greeting card, magnet, shirt, etc. with the content item printed on it, a printed or framed version of the content item, etc.). If the user chooses to share the content item, the application may direct the user to a user interface for selecting one or more applications to be utilized to share the content item, as illustrated in FIG. 13R. For instance, such applications may comprise text messaging, email, social networking site(s) (e.g., Facebook™, Twitter™, Google+™, etc.), and the like.

If a user selects input 1214, the application may direct the user to the user interface(s) in FIGS. 14A and 14B, which illustrate user interface(s) for setting user preferences. For example, the user interface may comprise inputs for enabling or disabling automatic facial or object recognition, enabling or disabling voice commands (e.g., capturing an image or video by speaking a word or phrase), enabling or disabling cloud synchronization (e.g., in which captured content items are automatically stored in cloud storage and/or in which content items in cloud storage are automatically synchronized with corresponding content items that are stored locally on the device), enabling or disabling geo-location (e.g., in which geo-location information is automatically associated as metadata with generated content items), enabling or disabling calendar synchronization (e.g., as performed by scheduling module 207), and/or enabling or disabling tagging (e.g., automatic tagging of objects, such as faces, pets, or landmarks, in a content item, as performed by modules 203 and/or 205). The user interface may also comprise inputs for utilizing additional services provided by or through the application, such as subscribing to cloud storage, purchasing more cloud storage, and/or subscribing to monthly gifts (e.g., images printed on physical objects, such as greeting cards, mugs, shirts, etc.). In addition, the user interface may comprise inputs for setting camera preferences, such as enabling or disabling a rapid burst mode, establishing a default naming preference (e.g., naming prefix to be used for captured images and/or videos), changing a brightness, and/or enabling or disabling a sound representing a closing shutter that may be played whenever a photograph is taken using the device. The user interface may also comprise inputs for creating a personal social network (e.g., a content gallery that can be viewed by one or more contacts of the user) and/or inviting contacts to join the personal social network (e.g., to browse and/or follow the content gallery).

Figure 15A:
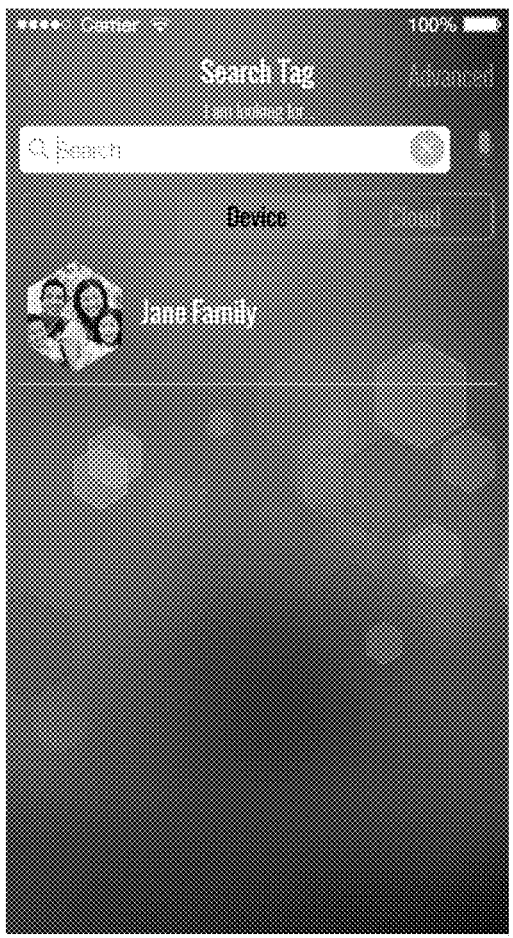
FIG. 15A-15B illustrate example user interfaces for searching content in an application that associates metadata with content items, according to an embodiment.
Figure 15B:
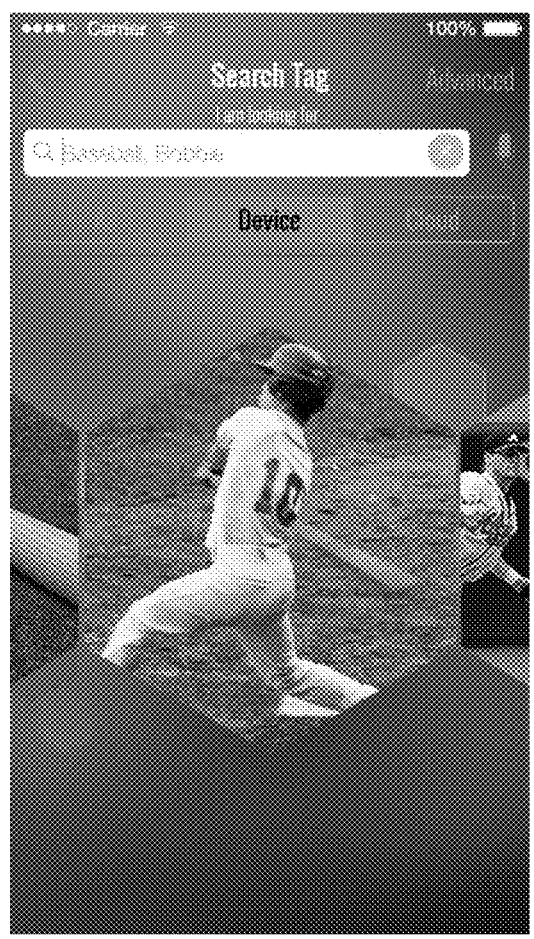

If a user selects input 1215, the application may direct the user to the user interface(s) in FIGS. 15A and 15B, which illustrate user interface(s) for searching the user's accessible content items. As shown in FIG. 15A, the application may provide a user interface with an input for inputting keywords to a search engine (e.g., the RCMS discussed elsewhere herein) that searches the metadata associated with user's locally and/or remotely stored content items. The user interface may allow a user to view, select, and/or search all content items or groups of content items (e.g., albums of content items) for the user. In addition, the user may be permitted to limit the viewing, selecting, and/or searching of content items based on where the content items are stored, e.g., locally on the device or remotely. For example, if the user selects an input corresponding to local storage (e.g., the input labeled "Device" in FIGS. 15A and 15B), only those content items or albums stored locally on the device will be displayed. If the user selects an input corresponding to remote storage (e.g., the input labeled "Cloud" in FIGS. 15A and 15B), only those content items or albums stored remotely (e.g., in cloud storage or on a server) will be displayed. On the other hand, if the user selects an input corresponding to all content items (e.g., the input labeled "All" in FIGS. 15A and 15B), all content items or albums, regardless of whether they are stored locally or remotely, will be displayed. If a user inputs search criteria (e.g., keywords) or selects an album (e.g., from the user interface illustrated in FIG. 15A), the application may display a user interface, such as the one illustrated in FIG. 15B, that allows a user to browse all of the content items that match the search criteria or that are in the album. In a touch-enabled device, the application may enable the user to browse the content items using any well-known touch operations (e.g., swiping, flicking, pinching, pulling, scrolling, etc.).

Figure 16A:
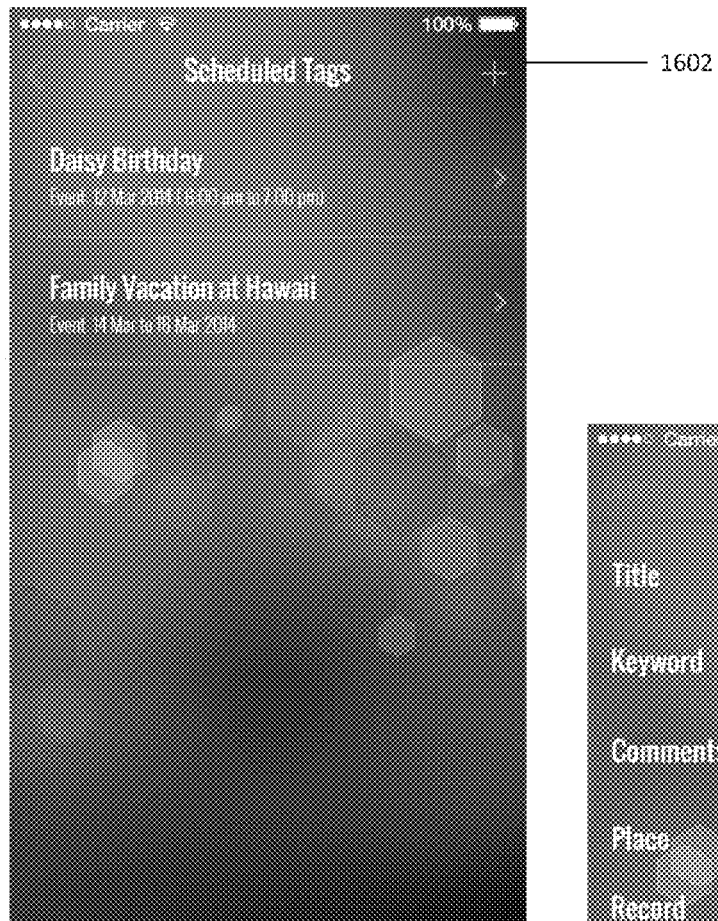
FIG. 16A-16B illustrate example user interfaces for scheduling metadata to be associated with content items, according to an embodiment.
Figure 16B:
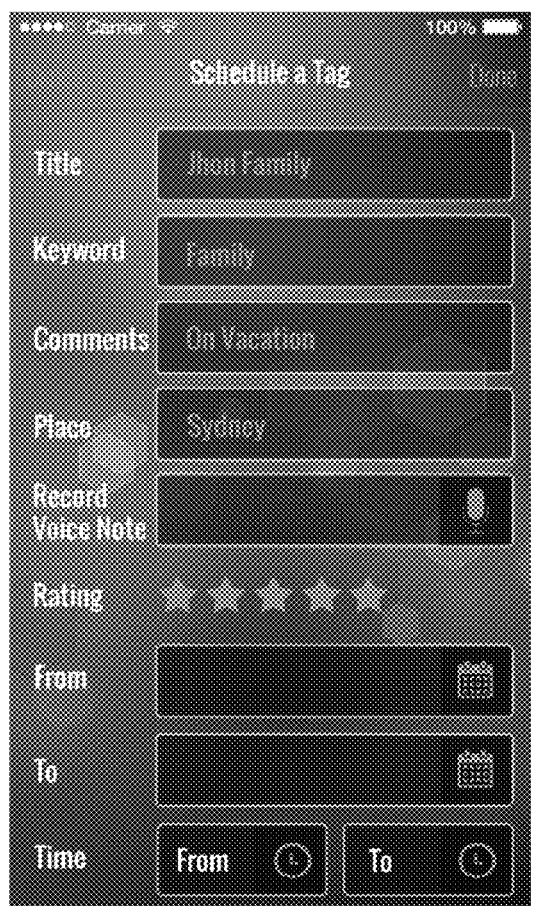
Figure 17A:
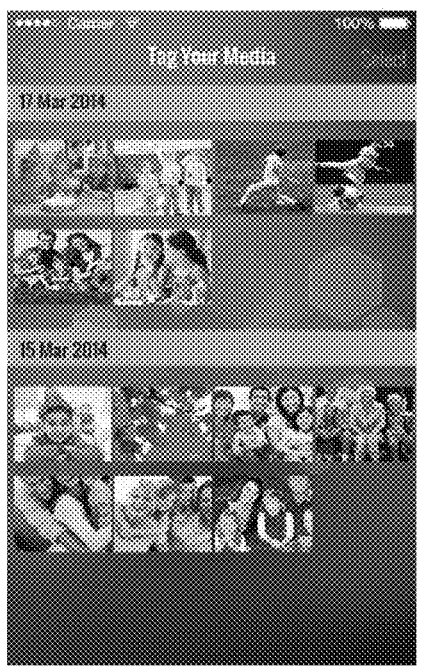
FIGS. 17A-17C illustrate example user interfaces for associating metadata with previously-generated content items, according to an embodiment.
Figure 17B:
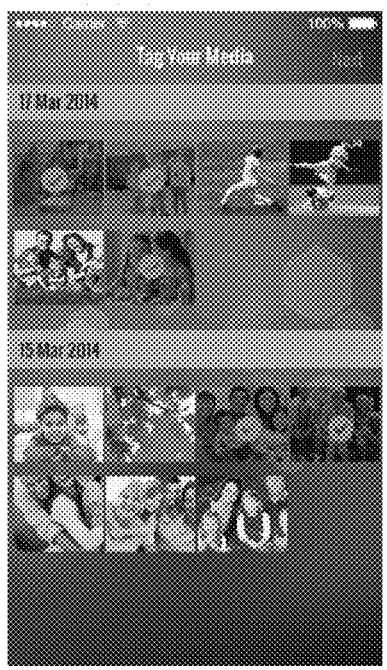
Figure 17C:
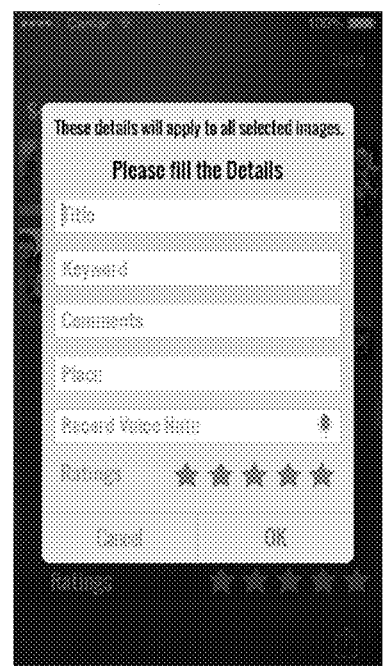

If a user selects input 1216, the application may direct the user to user interface(s) in FIGS. 16A and 16B, which may be provided by scheduling module 207 for defining scheduled metadata. As illustrated in FIG. 16A, the application may provide a user interface with a list of scheduled items defined by a time period (e.g., start time and end time) and metadata (e.g., a title, description, etc.). The user may select each scheduled item in the list, and, in response, the application may direct the user to a user interface for editing the scheduled item, such as the user interface illustrated in FIG. 16B. The user interface may also comprise an input 1602 for creating a new scheduled item, which also may result in the application directing the user to a user interface for editing a new scheduled item, as illustrated in FIG. 16B.

As illustrated in FIG. 16B, the user interface for creating or editing a scheduled item may comprise inputs for defining scheduled metadata (e.g., to be used by scheduling module 207). This user interface may be similar to the user interface in FIG. 13E. Such inputs may comprise inputs for receiving a title, keyword(s), comments, a location, an audio note, a rating, a start date and time, an end date and time, and/or the like, as well as saving the scheduled item.

If a user selects input 1217, the application may direct the user to user interface(s) in FIGS. 17A-17C for adding metadata to existing content items. As illustrated in FIG. 17A, the user may browse his or her content items, sorted, organized, arranged or filtered according to one or more criteria (e.g., creation date, content type, etc.). As illustrated in FIG. 17B, the user may select one or more of the content items (e.g., by touching them on a touch-enabled display, clicking them using a mouse or other pointing device, etc.), and click a "next" input to begin specifying metadata to be associated with the selected content item(s). Advantageously, the user may select a plurality of content items in order to specify metadata to be associated with them in bulk. As illustrated in FIG. 17C, after a user has selected the content item(s), the application may provide a user interface for inputting metadata to be associated with each of the selected content item(s). This user interface may be similar or identical to the user interface in 13E, and may comprise inputs for receiving a title, keyword(s), comments, a location, an audio note, a rating, and/or the like, as well as submitting the metadata for association with the selected content item(s). Once the user submits the metadata, the metadata may be associated with each of the content item(s) that the user selected in the user interface illustrated in FIG. 17B.

The user interfaces described above are merely illustrative. It should be understood that more, fewer, or different user interfaces may be used, that more, fewer, or different metadata may be collected and/or generated, and that more, fewer, or different tools and features may be provided.

For example, in an alternative embodiment, one or more of the user interfaces may overlay a primary user interface, such as by sliding a tab at a side of the primary user interface (e.g., at the bottom of a display screen) onto the primary user interface to expose a secondary user interface. In such an embodiment, the secondary user interface may be hidden again by sliding the tab back towards its original position. As one example, the user interface illustrated in FIG. 13A may be the primary user interface, and the lower and/or upper icon-populated portions of the user interface may be slid towards the middle of the screen to expose further user interfaces, such as the additional portions of one or more of the user interfaces illustrated in FIGS. 13E-13R or similar user interfaces.

In an embodiment, the user interfaces may be capable of being branded for a variety of different entities, markets, and/or purposes. For example, the user interfaces may be generated from templates (e.g., comprising tags, field, and/or placeholders) that are dynamically or statically populated with brand-specific elements, such as logos, colors, fonts, etc., and/or formatted according to brand-specific styles (e.g., style sheets, such as CSS). In this manner, the "skin" of the user interfaces can be changed to suit a particular entity, market, and/or purpose. For instance, an insurance company may want each of its claims adjusters to utilize the disclosed software application, for example, to capture photographs of property damage related to insurance claims. Thus, the insurance company may brand the software application with its logo, colors, etc. In an embodiment, the insurance company may even load the software application with preset metadata, related to the insurance company or its internal processes, to be automatically associated with content items captured using the software application.

2.3. Example Processes

Example processes—at least portions of which may be implemented by, or work in conjunction with, the disclosed software application—will now be described with reference to FIGS. 18-23, according to embodiments. These processes may include, or otherwise be used in conjunction with, the example user interfaces described above.

It should be understood that the software application may comprise both a mobile or client-side application (e.g., which executes on a mobile device) and a web or server-side application (e.g., a cloud-based application). Each of FIGS. 18-23 categorize each step based on the relevant actor (i.e., the user, the mobile application, the web application, or an ecommerce site). For example, in FIG. 18, steps 1802, 1804, 1806, 1812, 1820, 1840, 1842, and 1844 are shown as being performed by the mobile application, the remainder of the steps are shown as being performed by a user of the mobile application, and no steps are performed by the web application. However, for each of FIGS. 18-23, it should be understood that the various steps may be apportioned between the user, mobile application, web application, and ecommerce site in different combinations than those illustrated.

Figure 18:
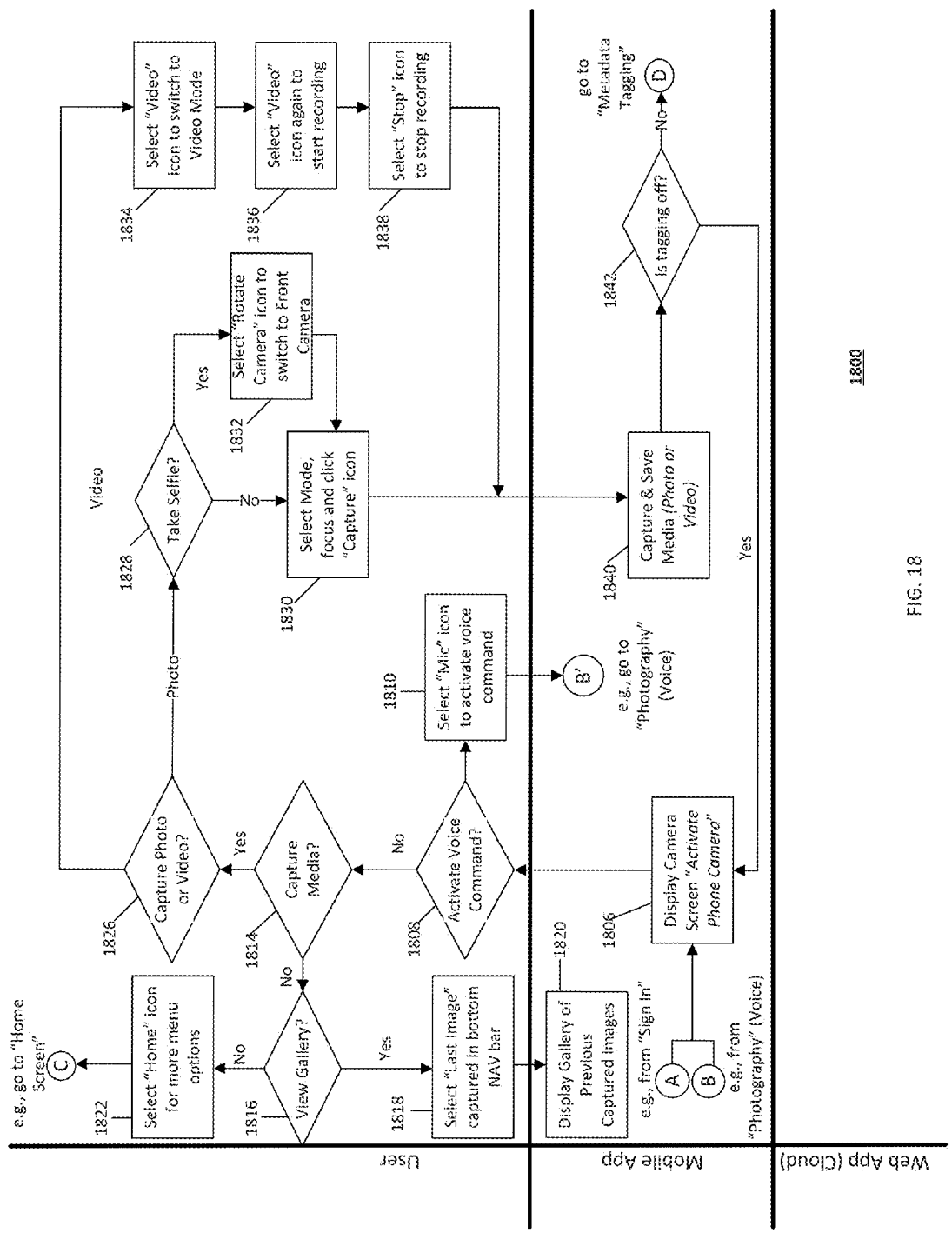
FIG. 18 illustrates an example process for capturing content without voice input, according to an embodiment.

FIG. 18 illustrates an example process 1800 for a photography mode without voice input, according to an embodiment. The mobile application may initiate process 1800 in response to a sign-in or other authentication or registration process (e.g., using the user interface(s) illustrated in FIGS. 11A-11C). Alternatively or additionally, the mobile application may initiate process 1800 in response to an input or other user operation, such as an operation that switches to process 1800 from process 1900, which is described in detail below with reference to in FIG. 19. In either case, in step 1806, the mobile application displays a camera screen or screens, such as the user interface illustrated in FIG. 12A.

In step 1808, the user determines whether or not to activate a voice input mode. If the user chooses to activate the voice input mode, the user performs an operation in step 1810, such as selecting a microphone icon or other input of a user interface displayed in step 1806. In response to the user operation received in step 1810, the mobile application initiates process 1900, which is a photography mode with voice input.

In step 1814, the user determines whether or not to capture a content item. If the user chooses not to capture a content item, in step 1816, the user may determine whether or not to view a gallery of one or more captured content items. If the user chooses to view the gallery, the user performs an operation in step 1818, such as selecting a thumbnail or other indication of the most recently captured content item or other input of a user interface displayed in step 1806. In response to the user operation received in step 1818, the mobile application displays a gallery of previously-captured content items in step 1820. On the other hand, if the user chooses not to view the gallery, the user may perform an operation in step 1822 to view more menu options (e.g., by selecting a home icon or other input of a user interface displayed in step 1806 to display the user interface illustrated in FIG. 12B). In response to the user operation received in step 1822, the mobile application may display a home screen or other user interface.

It should be understood that steps 1808, 1814, and 1816 may be performed in other combinations or orders than those depicted in FIG. 18. For example, these may be options selected by the user, using inputs of a user interface displayed in step 1806, in any arbitrary combination or order that the user desires.

If the user chooses to capture a content item, in step 1826, the user may determine what type of content item to capture (e.g., photograph or video). If the user chooses to capture a photograph, in step 1828, the user may determine whether or not to capture a "selfie" (i.e., a photograph of the user's self). If the user chooses not to capture a selfie, the user performs an operation in step 1830, which may comprise selecting a mode and/or focus, and/or selecting a capture icon or other input of a user interface displayed in step 1806. On the other hand, if the user chooses to capture a selfie, the user performs an operation in step 1832, such as selecting a rotate-camera icon or other input of a user interface displayed in step 1806, prior to performing the operation in step 1830. The operation performed in step 1832 may cause the mobile application to switch between a first camera that faces out from the back of a device (i.e., a back-facing camera generally used to capture images of subjects other than the user) to a second camera that faces out from the front of the device (i.e., a front-facing camera), such that the user can capture a photograph or video of himself or herself while simultaneously viewing the image(s) to be captured by the front-facing camera on a display of the device (e.g, a mobile phone or tablet computer).

If the user chooses to capture a video, the user performs an operation in step 1834, such as selecting a video icon or other input of a user interface displayed in step 1806. If the mobile application was previously in the photograph mode, in response to the operation in step 1834, the mobile application will switch to the video mode. Then the user may perform the same or similar operation in step 1836 (or, alternatively, a different operation, such as selecting a different input) to initiate video recording. In step 1838, the user may perform an operation (which may be the same or different than the operations performed in steps 1834 and/or 1836) to stop video recording.

It should be understood that, if the mobile application was already in video mode in step 1834, in response to the operation in step 1834, the mobile application would initiate video recording (such that step 1836 would be omitted). It should also be understood that between steps 1826 and 1828, if the mobile application was previously in video mode, a further operation (not shown) may be required to switch the mobile application to photograph mode.

When the content item has been captured via the operations in steps 1830 or 1838, the mobile application may save the content item in step 1840. In step 1842, the mobile application determines whether or not tagging is enabled. If tagging is enabled, the mobile application may initiate metadata tagging process 2000 (e.g., automatically or in response to a user operation), which is described in more detail below with reference to FIG. 20. Otherwise, if tagging is not enabled, the mobile application may return to step 1806.

Figure 19:
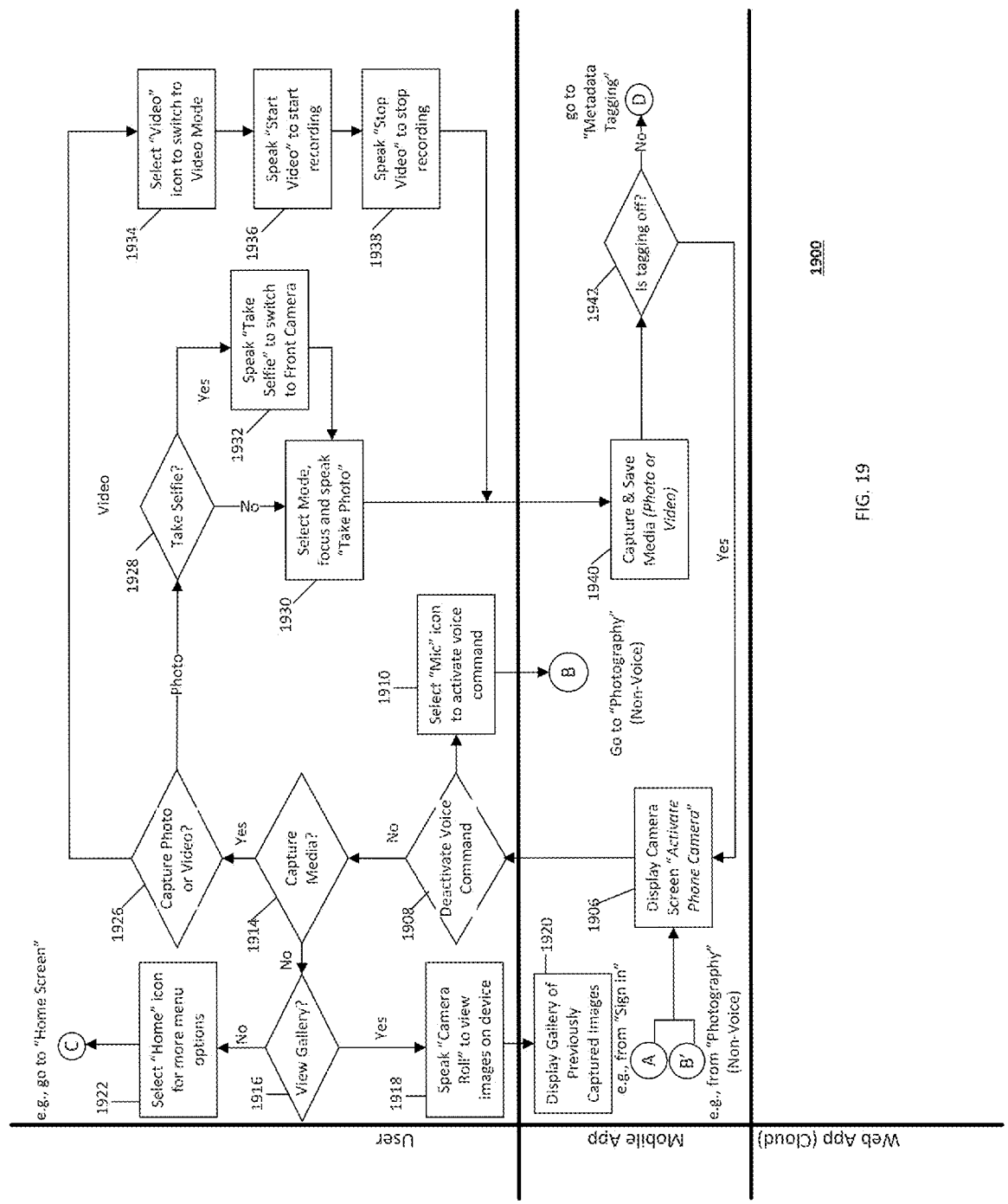
FIG. 19 illustrates an example process for capturing content with voice input, according to an embodiment.

FIG. 19 illustrates an example process 1900 for a photography mode with voice input, according to an embodiment. Process 1900 is nearly identical to process 1800 except that voice commands (e.g., a specific word or phrase spoken by the user into a microphone of the device executing the mobile application) are received and processed in place of one or more of the touch operations in process 1800. It should be understood that descriptions of elements in FIG. 18 that have corresponding reference numerals to elements in FIG. 19 (e.g., step 1806 in FIG. 18 correspond to step 1906 in FIG. 19) also apply to those elements with corresponding reference numerals in FIG. 19.

Thus, only the differences between processes 1900 and 1800 will be described with respect to FIG. 19. For example, in contrast to the mobile application initiating process 1800 in response to an operation that switches to process 1800 from process 1900, process 1900 may be initiated in response to an operation that switches to process 1900 from process 1800, as well as in response to any other operation or process. In addition, in step 1904, the mobile application initiates process 1800 in response to a user operation in step 1910 to deactivate the voice input mode (which, in turn, follows a user determination in step 1908 to deactivate the voice input mode), as opposed to the other way around in process 1800. Furthermore, the user's actions are the same in process 1900 as in process 1800, except that the inputs in steps 1918, 1930, 1932, 1936, and 1938 are voice commands as opposed to touch operations.

Figure 20B:
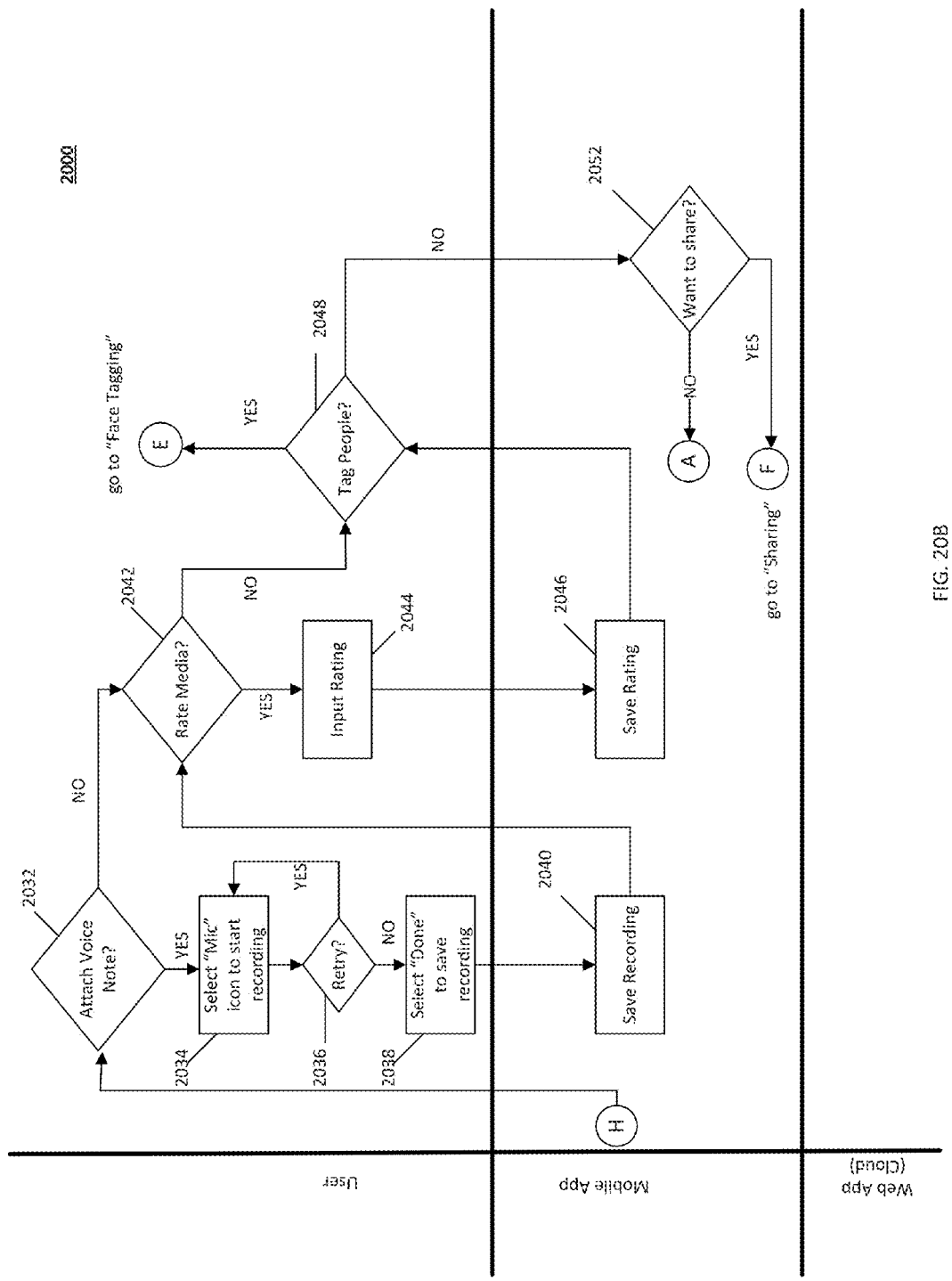

FIGS. 20A and 20B illustrate an example process 2000 for metadata tagging, according to an embodiment. As discussed above, process 2000 may be initiated if it is determined that tagging is enabled in step 1842 of process 1800 or step 1942 of process 1900. In step 2006, the mobile application displays a metadata details screen or screens, such as one or more of the user interfaces illustrated in FIGS. 13E-13K.

In step 2008, the user determines whether or not to tag the captured content (i.e., one or more captured content items) at the current time. If the user chooses not to tag the captured content at the current time, the user may then determine whether or not to disable tagging. If the user chooses not to disable tagging, the user performs an operation in step 2012, such as selecting a "tag later" indicator or other input of a user interface displayed in step 2006. In response to the user operation received in step 2012, the mobile application may apply default metadata in step 2014, and return to either process 1800 or process 1900 (or another depicted or non-depicted process).

On the other hand, if the user chooses to disable tagging, the user performs an operation in step 2018, such as selecting a "turn off tagging" indicator or other input of a user interface displayed in step 2006. In response to the user operation received in step 2018, the mobile application may turn off metadata tagging in step 2020, and proceed to step 2014.

If the user chooses to tag the captured content in step 2008, the user may then determine whether or not to tag the captured content using voice input in step 2022. If the user chooses to tag the captured content using voice input, the user performs an operation in step 2024, such as selecting a microphone icon or other input of a user interface displayed in step 2006, which enables the user to record audio (e.g., an oral, narrative description) to be used as metadata. In step 2026, the user may retry or re-record the audio one or more times until the user is satisfied with the recording. Once the user is satisfied with the recorded audio, in step 2028, the mobile application may save the audio recording or a transformation of the audio recording (e.g., text output from a voice-to-text process performed on the audio recording) as metadata to be associated with the captured content.

On the other hand, if the user chooses, in step 2022, to tag the captured content without using voice input, the user enters the metadata using input keys (e.g., of a virtual or hardware keyboard) in step 2030. In step 2028, the mobile application then saves the entered metadata in associated with the captured content, and proceeds to step 2032.

In step 2032, the user determines whether or not to attach a voice note to the captured content. If the user chooses to attach a voice note, the user performs an operation in step 2034, such as selecting a microphone icon or other input, and records a voice note. In step 2036, the user may retry or re-record the voice note one or more times until the user is satisfied with the recording. Once the user is satisfied with the recorded voice note, the user may perform an operation in step 2038 to indicate that the user is satisfied with the voice note. Accordingly, in step 2040, the mobile application saves the voice note in association with the captured content.

After the voice note has been saved in step 2040 or if the user chose not to attach a voice note in step 2032, in step 2042, the user determines whether or not to rate the captured content. If the user chooses to rate the captured content, the user performs an operation in step 2044 which indicates the user's rating, such as by selecting a star icon representative of a ranking on a scale from one to a predetermined number (e.g., five) of stars. In step 2046, the user's rating is saved in association with the captured content.

After the user's rating has been saved in step 2046 or if the user chose not to rate the captured content in step 2042, the user determines whether or not to tag objects (e.g., people, faces, landmarks, pets, etc.) in the captured content in step 2048. If the user chooses to tag objects, process 2000 may branch into process 2100, which is described in detail below with reference to FIG. 21.

On the other hand, if the user chooses not to tag objects, in step 2052, the mobile application may prompt the user as to whether or not the user wants to share the captured content. If the user chooses to share the captured content, process 2000 may branch into process 2200, which is described in detail below with reference to FIG. 22. Otherwise, if the user chooses not to share the captured content, process 2000 may return to either process 1800 or process 1900 (or another depicted or non-depicted process).

It should be understood that the determinations of whether or not to perform voice input in step 2022, attach a voice note in step 2032, rate the captured content in step 2042, and/or tag objects in step 2048 may be performed in any order, and are not limited to the order illustrated in FIG. 20. It should also be understood that these steps or sub-processes may be performed as part of a wizard (e.g., using multiple, sequential user interfaces) and/or may be performed at will in any arbitrary order through various user operations (e.g., by selecting inputs of a single user interface). As an example, step 2030 may be performed through the user interfaces illustrated in FIGS. 13E-13F, steps 2034-2038 may be performed through the user interfaces illustrated in FIGS. 13G-13J, and step 2044 may be performed through the user interface illustrated in FIG. 13E.

Figure 21:
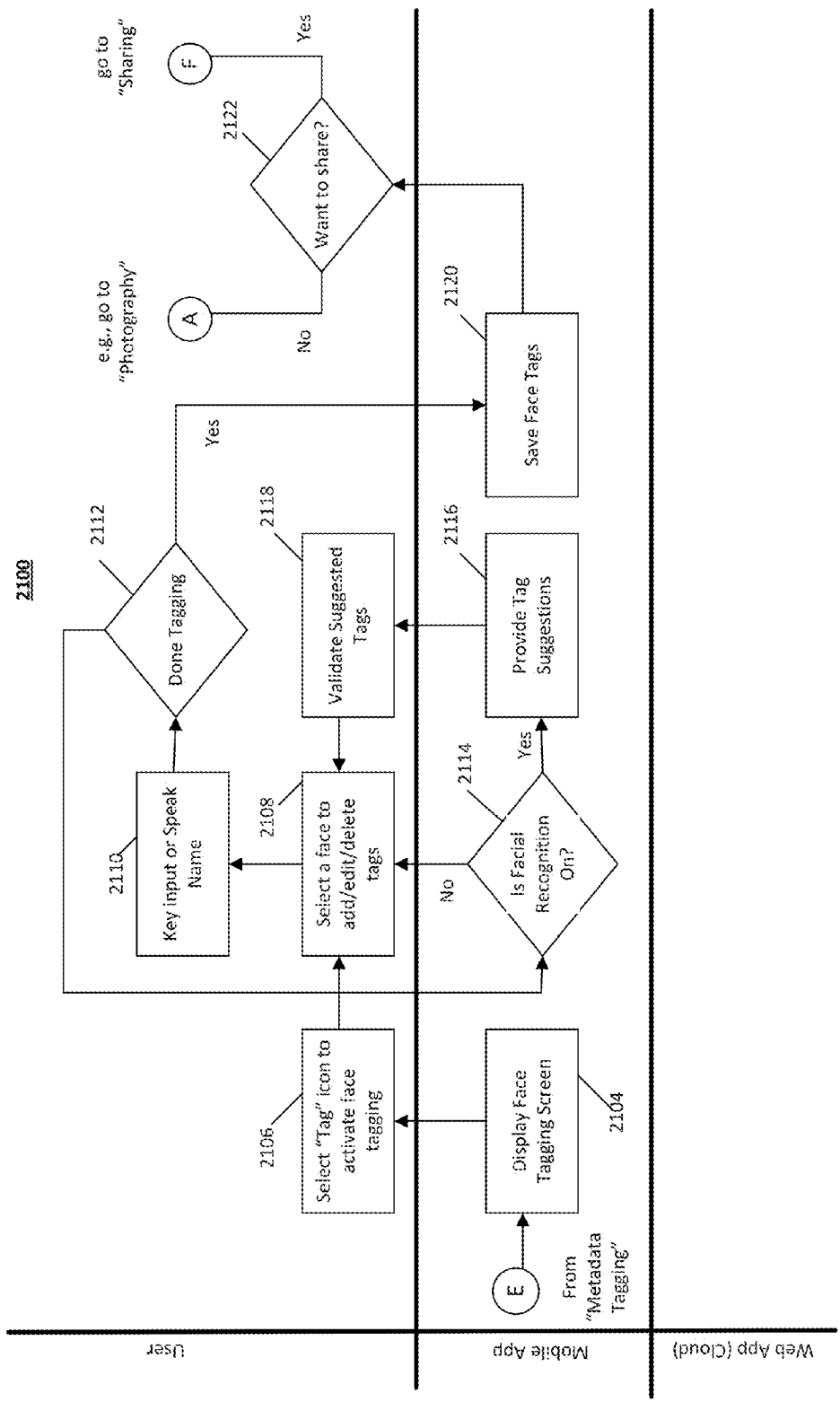
FIG. 21 illustrates an example process for facial recognition, according to an embodiment.

FIG. 21 illustrates an example process 2100 for tagging an object (e.g., person, face, pet, landmark, etc.) in captured content, according to an embodiment. As discussed with respect to FIG. 20, the mobile application may initiate process 2100 as a branch from process 2000 when the user chooses to tag people (or other types of objects). In step 2104, the mobile application displays an object-tagging screen, such as one or more of the user interfaces illustrated in FIGS. 13L-13P.

In step 2106, the user may perform an operation to activate tagging or a certain type of tagging (e.g., face tagging), such as by selecting a tag icon or other input of a user interface displayed in step 2104. In step 2108, the user may select an object, such as a face, in order to add, edit, or delete a tag associated with the object. For example, the mobile application may automatically recognize certain types of objects (e.g., face, pet, structure, etc.) and place a frame around the object, as illustrated in FIG. 13L according to one embodiment. Alternatively, the mobile application may allow the user to select any arbitrary object in the captured content (e.g., by tapping it, drawing a frame around it, etc.). In response to the user selection of an object, the mobile application may provide an input (e.g., textbox) for entering metadata (e.g., a name) to be associated with the selected object.

In step 2110, the user may input metadata (e.g., a name) to be associated with the selected object. This input may be performed manually (e.g., through a virtual or hardware keyboard) or via voice input (as described elsewhere herein). In step 2112, the user determines whether or not the user is done tagging objects. If so, in step 2120, the tags are saved in association with their respective objects (e.g., in association with coordinates associated with the objects) in the captured content. Otherwise, the mobile application determines in step 2114 whether or not automatic recognition (e.g., facial recognition) is enabled. Notably, in alternative embodiments of process 2100, step 2106 may also proceed to step 2114 instead of to step 2108.

In step 2114, if the mobile application determines that automatic recognition is not enabled, process 2100 proceeds to step 2108 in which tags may be manually entered by the user. Otherwise, if the mobile application determines that automatic recognition is enabled, process 2100 proceeds to step 2116, in which object recognition, such as facial recognition, is performed (as described elsewhere herein), and suggested tags are provided to the user (e.g., by superimposing metadata, such as names, next to recognized objects, such as faces of people, pets, landmarks, etc.). In step 2118, the user may review the suggested tags to validate them or edit or delete them in step 2108.

Once tagging had been completed and the tags have been saved in step 2120, the user may determine whether or not to share the tagged content in step 2122. If the user chooses not to share the tagged content, process 2100 may return to either process 1800 or 1900 (or another depicted or non-depicted process). On the other hand, if the user chooses to share the tagged content, process 2100 may branch to process 2200, which is described in detail below with reference to FIG. 22.

Figure 22:
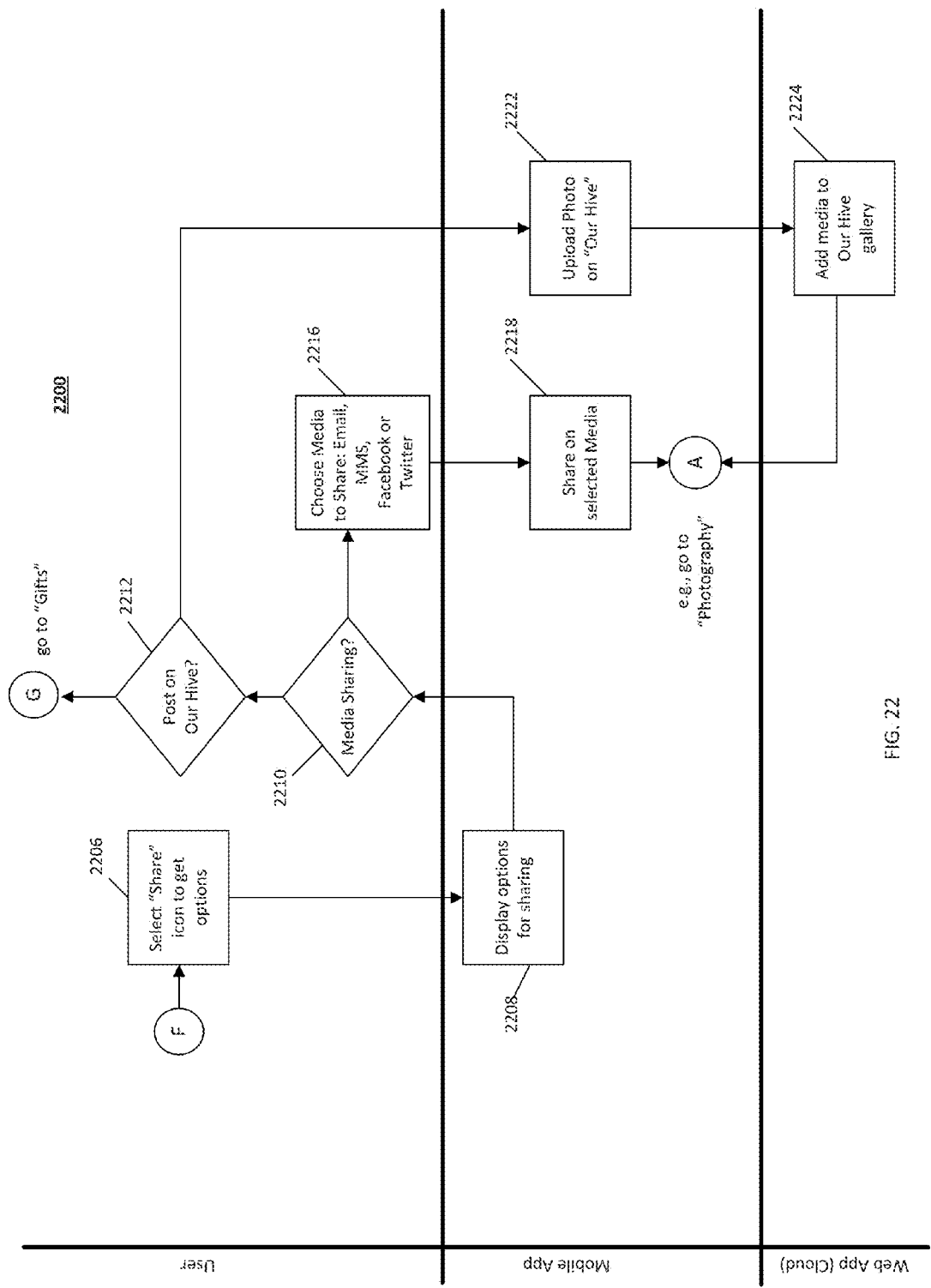
FIG. 22 illustrates an example process for sharing captured content, according to an embodiment.

FIG. 22 illustrates an example process 2200 for sharing captured content, according to an embodiment. As discussed above, the mobile application may initiate process 2200 from process 2000 or process 2100 (or another depicted or non-depicted process). In step 2206, the user may perform a user operation to initiate process 2200, such as selecting a share icon or other input of a user interface (e.g., the user interface illustrated in FIG. 13Q). In step 2208, the mobile application displays sharing options to the user (e.g., using the user interface illustrated in FIG. 13R).

In step 2210, the user determines whether or not to utilize a sharing medium, such as email, text message (e.g., Short Message Service (SMS), Multimedia Messaging Service (MMS), etc.), or one or more social networks (e.g, Facebook™, Twitter™, Google+™, Instagram™, etc.). If the user chooses to utilize a sharing medium, the user selects the sharing medium or media from a plurality of sharing media options (e.g., as illustrated in FIG. 13R) in step 2216. In step 2218, the captured (and optionally tagged) content is then shared.

On the other hand, if the user chooses not to utilize a sharing medium in step 2210, the user may determine whether or not to post the captured content to a gallery (e.g., cloud-based gallery) in step 2212. If the user chooses not to post the captured content to the gallery, process 2200 may branch to process 2300, which is described in detail below with reference to FIG. 23. However, if the user chooses to post the captured content to the gallery, the user performs an operation in step 2222, such as selecting a post icon or other input (e.g., from the user interface illustrated in FIG. 13Q). Then, in step 2224, the captured content is received by the web application (e.g., a cloud-based application) over one or more networks and stored in memory that is remote from the device on which the mobile application is executing.

It should be understood that steps 2210, 2212, and 2214 may be performed in a different combination and/or order than illustrated in FIG. 22, and that the combination and/or order may be chosen by the user. For example, the user may depress one or more of the buttons illustrated in FIG. 13Q to share the captured content, post the captured content to a cloud-based gallery, and/or create a gift using the captured content, in any arbitrary combination and/or order which the user desires.

Figure 23:
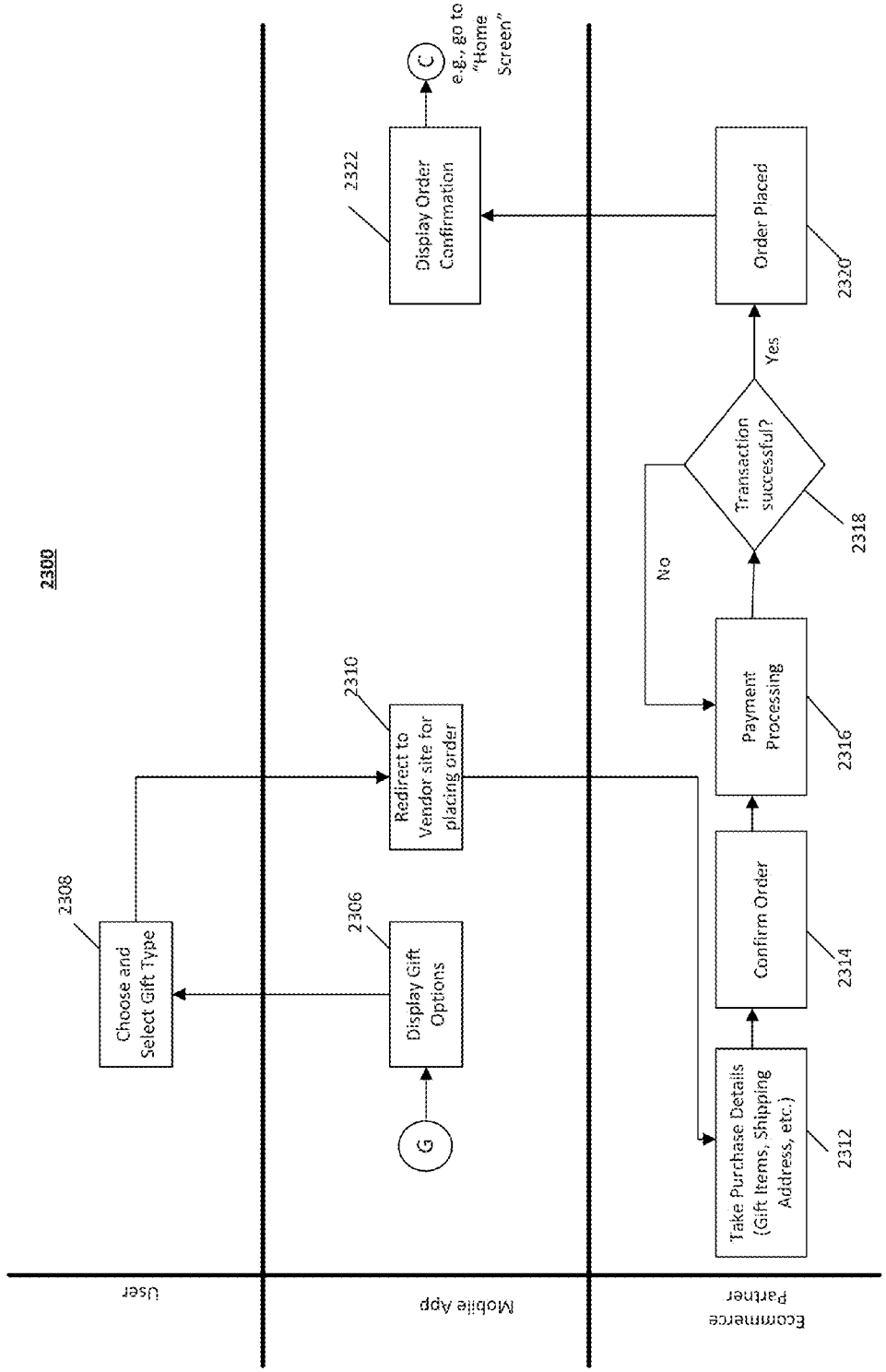
FIG. 23 illustrates an example process for creating and purchasing a gift comprising the captured content, according to an embodiment.

FIG. 23 illustrates an example process 2300 for creating a gift using captured content, according to an embodiment. As illustrated, process 2300 may be connected to process 2200 via process connection G. However, it should be understood that process 2300 may, alternatively or additionally, be connected to one or more other depicted or non-depicted processes (e.g., a preference-setting process).

Process 2300 begins in step 2306, in which the mobile application displays a user interface for selecting a gift option from one or a plurality of gift options. For example, the user interface may comprise a plurality of gift types that can be created using the captured content. In step 2308, the user selects a gift or gift type from the gift option(s).

In step 2310, the mobile application may direct the user to an ecommerce site for placing an order (e.g., a third-party vendor website, a website provided by the provider of the mobile application, etc.). Alternatively, the mobile application may itself provide the user interface(s) for placing the order and communicate over a network (e.g., the Internet) with a web service at the ecommerce site to consummate the transaction.

In step 2312, the ecommerce site receives order information, such as the gift item or type, shipping address, payment information, etc. The order information may be provided by the user and/or the mobile application. For example, the mobile application may store information to be used in the order information for the user, such as the user's shipping address, user's payment information, user identifier, and/or the like, and combine this stored information with the selected gift type, the captured content, and/or the like (with or without user input) to create the order information which is then transmitted (e.g., via a wireless network, the Internet, etc.) to the ecommerce site. Alternatively, some of this information (e.g., shipping address, payment information, etc.) may be stored at the ecommerce site and associated with the order information via an identifier included in the order information (e.g., a user identifier that uniquely identifies the user of the mobile application).

In any case, in step 2314, the order is confirmed (e.g., by providing a user interface to the user that comprises an order summary and input for confirming the order). In step 2316, the payment is processed using the payment information supplied by the user or mobile application or stored at the ecommerce site, and it is determined whether the payment was successful in step 2318. If the payment is not successfully processed, the ecommerce site may prompt or initiate prompting (e.g., via the mobile application) of the user to provide additional or different payment information. On the other hand, if the payment is successfully processed, in step 2320, the order is placed or completed. In step 2322, the mobile application may display a confirmation that the order was placed. After the user has viewed the confirmation, the mobile application may return to a home screen or other user interface.

3. System Overview

Figure 24:
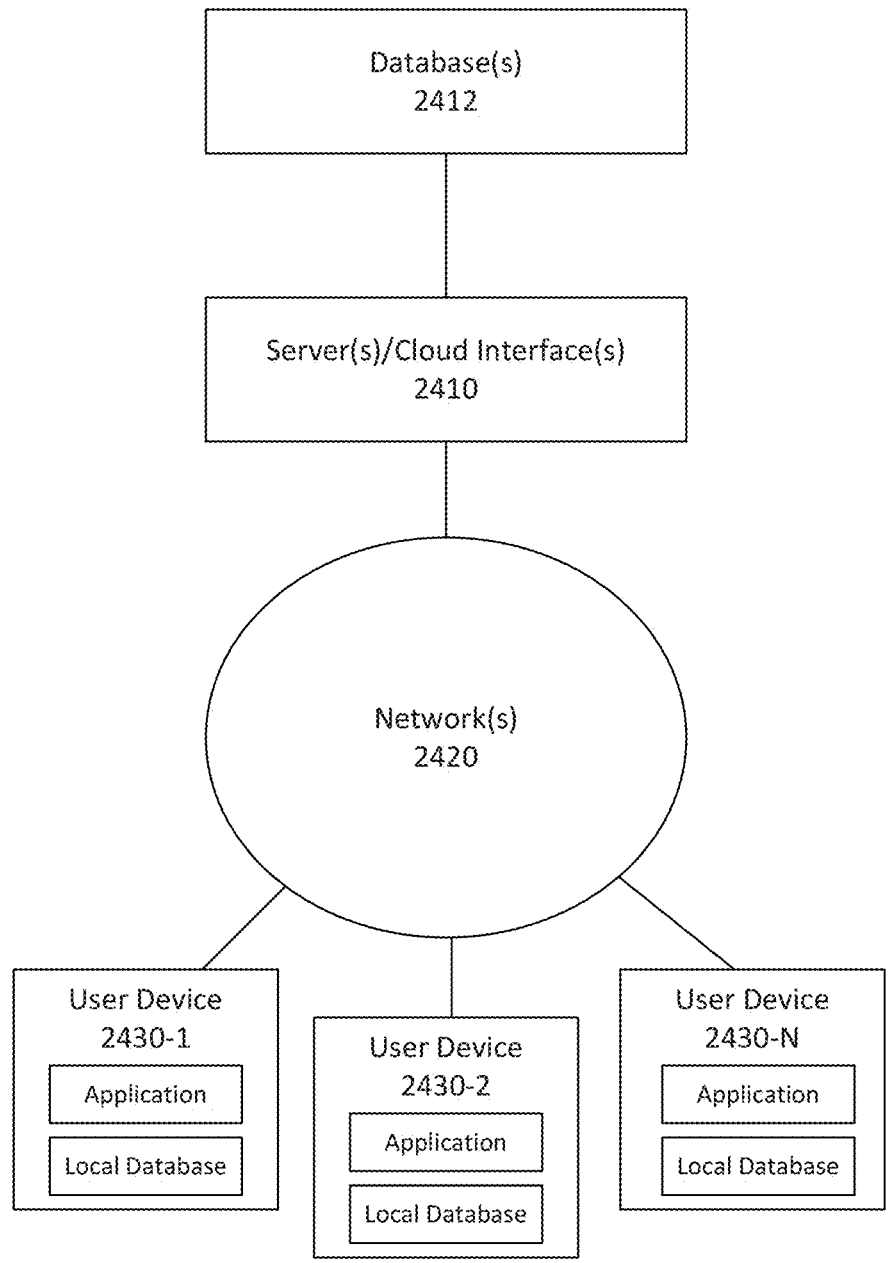
FIG. 24 illustrates an environment in which an application that associates metadata with content items may operate, according to an embodiment.

FIG. 24 illustrates an example system infrastructure in which the disclosed application may operate, according to an embodiment. The system may comprise a set of one or more servers or cloud interfaces or instances, which utilize shared resources of one or more servers (any of which may be referred to herein as a "platform" 2410) and one or more user devices which host and/or execute one or more of the various functions, processes, methods, and/or software modules described herein. User system(s) 2430 may host at least some modules of the application, according to embodiments disclosed herein, and/or a local database. Platform 2410 may be communicatively connected to the user system(s) 2430 via one or more network(s) 2420 and may also be communicatively connected to one or more database(s) 2412 (e.g., via one or more network(s), such as network(s) 2420) and/or may comprise one or more database(s) 2412. Network(s) 2420 may comprise the Internet, and platform 2410 may communicate with user system(s) 2430 through the Internet using standard transmission protocols, such as HyperText Transfer Protocol (HTTP), Secure HTTP (HTTPS), File Transfer Protocol (FTP), FTP Secure (FTPS), Secure Shell FTP (SFTP), and the like, as well as proprietary protocols. It should be understood that the components (e.g., servers and/or other resources) of platform 2410 may be, but are not required to be, collocated. Furthermore, while platform 2410 is illustrated as being connected to various systems through a single set of network(s) 2420, it should be understood that platform 2410 may be connected to the various systems via different sets of one or more networks. For example, platform 2410 may be connected to a subset of user systems 2430 via the Internet, but may be connected to one or more other user systems 2430 via an intranet. It should also be understood that user system(s) 2430 may comprise any type or types of computing devices, including without limitation, desktop computers, laptop computers, tablet computers, smart phones or other mobile phones, servers, game consoles, televisions, set-top boxes, electronic kiosks, and the like. While it is contemplated that such devices are capable of wired or wireless communication, this is not a requirement for all embodiments. In addition, while only a few user systems 2430, one platform 2410, and one set of database(s) 2412 are illustrated, it should be understood that the network may comprise any number of user systems, sets of platform(s), and database(s).

Platform 2410 may comprise web servers which host one or more websites or web services. In embodiments in which a website is provided, the website may comprise one or more user interfaces, including, for example, webpages generated in HTML or other language. Platform 2410 transmits or serves these user interfaces as well as other data (e.g., a downloadable copy of or installer for the disclosed application) in response to requests from user system(s) 2430. In some embodiments, these user interfaces may be served in the form of a wizard, in which case two or more user interfaces may be served in a sequential manner, and one or more of the sequential user interfaces may depend on an interaction of the user or user system with one or more preceding user interfaces. The requests to platform 2410 and the responses from platform 2410, including the user interfaces and other data, may both be communicated through network(s) 2420, which may include the Internet, using standard communication protocols (e.g., HTTP, HTTPS). These user interfaces or web pages, as well as the user interfaces provided by the disclosed application executing on a user system 2430, may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases that are locally and/or remotely accessible to user system(s) 2430 and/or platform 2410.

Platform 2410 may further comprise, be communicatively coupled with, or otherwise have access to one or more database(s) 2412. For example, platform 2410 may comprise one or more database servers which manage one or more databases 2412. A user system 2430 or application executing on platform 2410 may submit data (e.g., user data, form data, etc.) to be stored in the database(s) 2412, and/or request access to data stored in such database(s) 2412. Any suitable database may be utilized, including without limitation MySQL™, Oracle™, IBM™, Microsoft SQL™, Sybase™, Access™, and the like, including cloud-based database instances and proprietary databases. Data may be sent to platform 2410, for instance, using the well-known POST request supported by HTTP, via FTP, etc. This data, as well as other requests, may be handled, for example, by server-side web technology, such as a servlet or other software module, executed by platform 2410.

In embodiments in which a web service is provided, platform 2410 may receive requests from user system(s) 2430, and provide responses in eXtensible Markup Language (XML) and/or any other suitable or desired format. In such embodiments, platform 2410 may provide an application programming interface (API) which defines the manner in which user system(s) 2430 may interact with the web service. Thus, user system(s) 2430, which may themselves be servers, can define their own user interfaces, and rely on the web service to implement or otherwise provide the backend processes, methods, functionality, storage, etc., described herein. For example, in such an embodiment, a client application (e.g., the disclosed application) executing on one or more user system(s) 2430 may interact with a server application executing on platform 2410 to execute one or more or a portion of one or more of the various functions, processes, methods, and/or software modules described herein. The client application may be "thin," in which case processing is primarily carried out server-side by platform 2410. A basic example of a thin client application is a browser application, which simply requests, receives, and renders web pages at user system(s) 2430, while platform 2410 is responsible for generating the web pages and managing database functions. Alternatively, the client application may be "thick," in which case processing is primarily carried out client-side by user system(s) 2430. It should be understood that the client application may perform an amount of processing, relative to platform 2410, at any point along this spectrum between "thin" and "thick," depending on the design goals of the particular implementation. In any case, the application, which may wholly reside on either platform 2410 or user system(s) 2430 or be distributed between platform 2410 and user system(s) 2430, can comprise one or more executable software modules that implement one or more of the processes, methods, or functions of the application(s) described herein.

4. Example Processing Device

Figure 25:
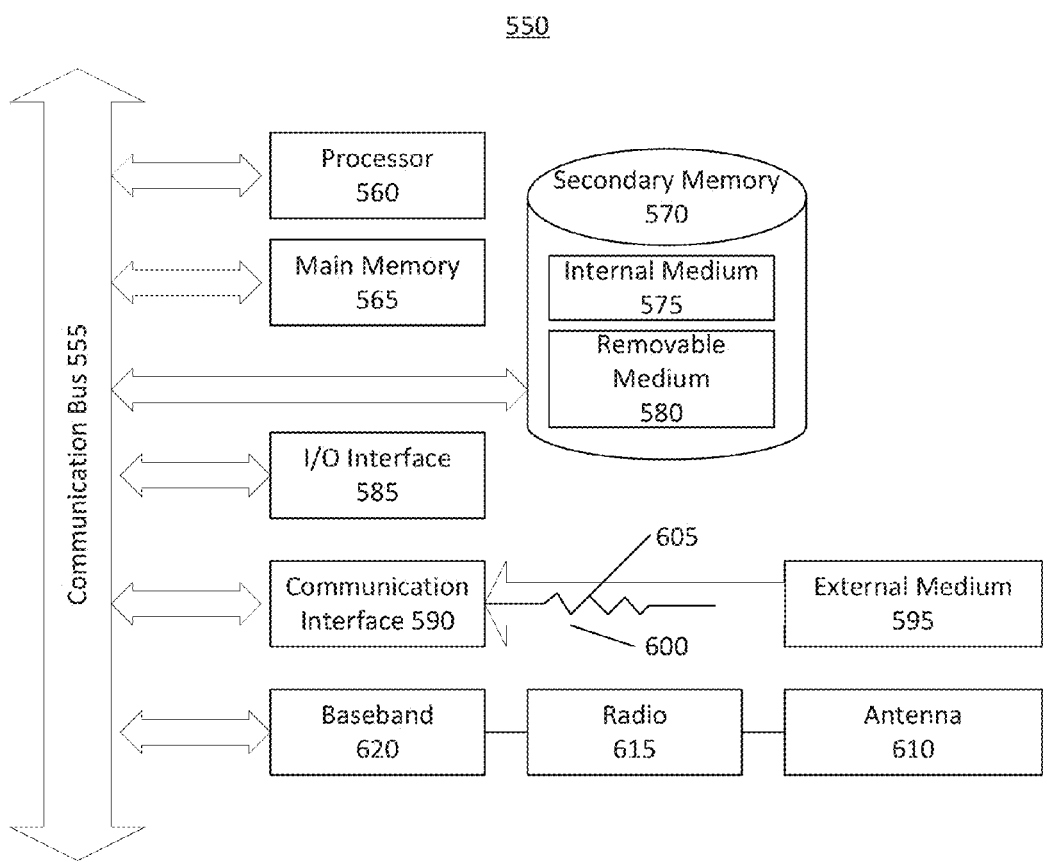
FIG. 25 illustrates a processing system on which one or more of the processes described herein may be executed, according to an embodiment.

FIG. 25 is a block diagram illustrating an example wired or wireless system 550 that may be used in connection with various embodiments described herein. For example the system 550 may be used as or in conjunction with one or more of the mechanisms, processes, methods, or functions (e.g., to store and/or execute the application or one or more software modules of the application) described above, and may represent components of platform 2410, user system(s) 2430, and/or other devices described herein. The system 550 can be a server or any conventional personal computer, or any other processor-enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Perl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block-oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software, such as the disclosed application) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method for scheduling the association of metadata with content, the method comprising using at least one hardware processor of a device to:
    at a first time,
        obtain event information from a virtual calendar, wherein the event information comprises at least one event detail and one or more parameters defining a future time period that is subsequent to the first time, and wherein the future time period represents a time at which an event represented by the event information is to occur,
        generate first event metadata based on the at least one event detail, and
        store the first event metadata, in association with the future time period, in a memory; and,
    subsequently, during the future time period which represents the time at which the event is to occur,
        retrieve the first event metadata from the memory, and
        associate the first event metadata with each of one or more content items generated on the device during the future time period.

2. The method of claim 1, wherein the one or more content items comprise a plurality of content items, and wherein the first event metadata is associated with each of the plurality of content items generated on the device during the future time period.

3. The method of claim 1, wherein the at least one event detail comprises a location.

4. The method of claim 1, wherein the at least one event detail comprises one or more participants.

5. The method of claim 1, comprising automatically periodically obtaining the event information from the virtual calendar.

6. The method of claim 5, wherein the virtual calendar is a third-party calendar application, and wherein the method comprises obtaining the event information from the third-party calendar application using an application programming interface.

7. The method of claim 1, further comprising using the at least one hardware processor of the device to:
    receive audio information using a microphone of the device;
    convert the audio information into text;
    generate second metadata based on the text; and
    associate the second metadata with the one or more content items.

8. The method of claim 7, comprising receiving the audio information while the one or more content items are generated.

9. The method of claim 1, further comprising using the at least one hardware processor of the device to:
    detect an object in the one or more content items by matching one or more features of the one or more content items to a stored representation of the object;
    retrieve object metadata associated with the stored representation of the object; and
    associate the object metadata with the one or more content items.

10. The method of claim 9, wherein matching one or more features of the one or more content items to a stored representation of the object comprises:
    determining a geo-location of the device; and
    comparing a representation of the one or more features to a plurality of representations of objects associated with the determined geo-location.

11. The method of claim 9, wherein the object is a face.

12. The method of claim 9, wherein the object is a pet.

13. The method of claim 9, wherein the object is a landmark.

14. The method of claim 1, further comprising using the at least one hardware processor of the device to:
    receive biometric information from a user of the device;
    generate authorship metadata based on the biometric information; and
    associate the authorship metadata with the one or more content items.

15. The method of claim 1, using the at least one hardware processor to:
    obtain location information representing a current location of the device;
    retrieve second metadata associated with the obtained location information; and
    associate the second metadata with one or more content items generated on the device.

16. The method of claim 15, wherein retrieving the second metadata associated with the obtained location information comprises:
    accessing a database comprising a plurality of records, wherein each of the plurality of records comprises location information and associated metadata;
    searching the database to identify at least one of the plurality of records that comprises location information matching the obtained location information; and
    determining the second metadata based on the associated metadata in the identified at least one record.

17. The method of claim 16, further comprising using the at least one hardware processor to:
    receive location information;
    receive metadata from a user of the device; and
    store the received location information and received metadata as one of the plurality of records in the database.

18. The method of claim 15, wherein retrieving the second metadata associated with the obtained location information comprises:
    accessing contact information associated with a user of the device, wherein the contact information comprises a plurality of contact records, and wherein each of the plurality of contact records represents a contact of the user and comprises location information for the contact;
    searching the contact information to identify a contact record that comprises location information matching the obtained location information; and
    determining the second metadata based on the identified contact record.

19. The method of claim 1, wherein the event is a first event and the future time period is a first future time period, and wherein the method further comprises:
  obtaining second event information from the virtual calendar, wherein the second event information comprises at least one second event detail and one or more second parameters defining a second future time period, wherein the second future time period represents a time at which a second event represented by the second event information is to occur;
  generating second event metadata based on the at least one second event detail;
  storing the second event metadata, in association with the second future time period, in the memory; and,
  subsequently, during the second future time period which represents the time at which the second event is to occur,
    retrieving the second event metadata from the memory, and
    associating the second event metadata with each of one or more content items generated on the device during the second future time period.

20. The method of claim 19, wherein at least a portion of the second future time period is within the first future time period, such that both the first event metadata and the second event metadata are associated with each of the one or more content items generated on the device during the at least a portion of the second future time period.

21. A non-transitory computer-readable medium having one or more sequences of instructions stored therein, wherein the one or more sequences of instructions, when executed by a processor of a device, cause the processor to:
  at a first time,
    obtain event information from a virtual calendar, wherein the event information comprises at least one event detail and one or more parameters defining a future time period that is subsequent to the first time, and wherein the future time period represents a time at which an event represented by the event information is to occur,
    generate first event metadata based on the at least one event detail, and
    store the first event metadata, in association with the future time period, in a memory; and,
  subsequently, during the future time period which represents the time at which the event is to occur,
    retrieve the first event metadata from the memory, and
    associate the first event metadata with each of one or more content items generated on the device during the future time period.

22. The non-transitory computer-readable medium of claim 21, wherein the one or more content items comprise a plurality of content items, and wherein the first event metadata is associated with each of the plurality of content items generated on the device during the future time period.

23. The non-transitory computer-readable medium of claim 21, wherein the one or more sequences of instructions further cause the processor to:
  receive audio information using a microphone of the device;
  convert the audio information into text;
  generate second metadata based on the text; and
  associate the second metadata with the one or more content items.

24. The non-transitory computer-readable medium of claim 21, wherein the one or more sequences of instructions further cause the processor to:
  detect an object in the one or more content items by matching one or more features of the one or more content items to a stored representation of the object;
  retrieve object metadata associated with the stored representation of the object; and
  associate the object metadata with the one or more content items.

25. A system for scheduling the association of metadata with content, the system comprising:
  at least one hardware processor;
  a memory; and
  one or more software modules that, when executed by the at least one hardware processor,
    at a first time,
      obtain event information from a virtual calendar, wherein the event information comprises at least one event detail and one or more parameters defining a future time period that is subsequent to the first time, and wherein the future time period represents a time at which an event represented by the event information is to occur,
      generate first event metadata based on the at least one event detail, and
      store the first event metadata, in association with the future time period, in the memory, and,
    subsequently, during the future time period which represents the time at which the event is to occur,
      retrieve the first event metadata from the memory, and
      associate the first event metadata with each of one or more content items generated by the system during the future time period.

26. The system of claim 25, wherein the one or more content items comprise a plurality of content items, and wherein the first event metadata is associated with each of the plurality of content items generated by the system during the future time period.

* * * * *